(12) United States Patent
Fuller et al.

(10) Patent No.: US 9,849,282 B2
(45) Date of Patent: Dec. 26, 2017

(54) PROPHYLACTIC BACTERICIDAL MEDICAL DEVICE

(71) Applicant: Aionx Antimicrobial Technologies, Inc., Boalsburg, PA (US)

(72) Inventors: Thomas A. Fuller, State College, PA (US); Richard A. Wysk, Raleigh, NC (US); Wayne J. Sebastianelli, Boalsburg, PA (US)

(73) Assignee: Aionx Antimicrobial Technologies, Inc., Boalsburg, PA (US)

( * ) Notice: Subject to any disclaimer, the term of this patent is extended or adjusted under 35 U.S.C. 154(b) by 0 days.

(21) Appl. No.: 15/216,197

(22) Filed: Jul. 21, 2016

(65) Prior Publication Data

US 2016/0325094 A1 Nov. 10, 2016

Related U.S. Application Data

(63) Continuation of application No. 14/644,497, filed on Mar. 11, 2015, now Pat. No. 9,421,285, which is a
(Continued)

(51) Int. Cl.
*A61N 1/00* (2006.01)
*A61N 1/30* (2006.01)
(Continued)

(52) U.S. Cl.
CPC ................ *A61N 1/30* (2013.01); *A61B 17/86* (2013.01); *A61B 17/864* (2013.01);
(Continued)

(58) Field of Classification Search
CPC ....... A61B 17/866; A61B 17/58; A61L 27/34; A61L 2/0082; A61F 2/0077; A61N 1/18
See application file for complete search history.

(56) References Cited

U.S. PATENT DOCUMENTS 2,655,922 A 10/1953 Knappwost
3,954,407 A 5/1976 Andary
(Continued)

FOREIGN PATENT DOCUMENTS

JP 10-505248 A 5/1998
JP 2000-510713 A 8/2000
(Continued)

OTHER PUBLICATIONS

Colomano, C. et al. "Activation of Antibacterial Silver Coatings on Surgical Implants by Direct Current: Preliminary Studies in Rabbits", Am J Vet Res., Jun. 1980, pp. 964-966, 41(6).
(Continued)

*Primary Examiner* — Robert N Wieland
(74) *Attorney, Agent, or Firm* — Patterson Thuente Pedersen, P.A.

(57) ABSTRACT

A medical implant system is described for inhibiting infection associated with a joint prosthesis implant. An inventive system includes an implant body made of a biocompatible material which has a metal component disposed on an external surface of the implant body. A current is allowed to flow to the metal component, stimulating release of metal ions toxic to microbes, such as bacteria, protozoa, fungi, and viruses. One detailed system is completely surgically implantable in the patient such that no part of the system is external to the patient while the system is in use. In addition, externally controlled devices are provided which allow for modulation of implanted components.

17 Claims, 7 Drawing Sheets

Related U.S. Application Data continuation of application No. 14/090,699, filed on Nov. 26, 2013, now Pat. No. 9,008,770, which is a continuation of application No. 13/417,269, filed on Mar. 11, 2012, now Pat. No. 8,620,431, which is a continuation of application No. 11/922,979, filed on Mar. 6, 2009, now Pat. No. 8,135,466, which is a continuation-in-part of application No. 11/172,138, filed as application No. PCT/US2006/026000 on Jun. 30, 2006, now abandoned.

(60) Provisional application No. 60/708,320, filed on Aug. 15, 2005.

(51) Int. Cl.

| | | |
|---|---|---|
| *A61B 17/86* | (2006.01) | |
| *A61F 2/30* | (2006.01) | |
| *A61F 2/36* | (2006.01) | |
| *A61L 27/30* | (2006.01) | |
| *A61L 27/54* | (2006.01) | |
| *A61N 1/20* | (2006.01) | |
| *A61L 2/00* | (2006.01) | |
| *A61N 1/18* | (2006.01) | |
| *A61B 17/60* | (2006.01) | |
| *A61B 17/00* | (2006.01) | |
| *A61F 2/00* | (2006.01) | |
| *A61F 2/32* | (2006.01) | |
| *A61F 2/34* | (2006.01) | |
| *A61F 2/28* | (2006.01) | |
| *A61F 2/48* | (2006.01) | |

(52) U.S. Cl.
CPC ........ *A61B 17/866* (2013.01); *A61B 17/8685* (2013.01); *A61F 2/0077* (2013.01); *A61F 2/28* (2013.01); *A61F 2/30* (2013.01); *A61F 2/30767* (2013.01); *A61F 2/36* (2013.01); *A61F 2/3609* (2013.01); *A61F 2/3676* (2013.01); *A61L 2/0082* (2013.01); *A61L 27/30* (2013.01); *A61L 27/306* (2013.01); *A61L 27/54* (2013.01); *A61N 1/00* (2013.01); *A61N 1/18* (2013.01); *A61N 1/20* (2013.01); *A61B 17/60* (2013.01); *A61B 2017/00734* (2013.01); *A61F 2/0095* (2013.01); *A61F 2/30724* (2013.01); *A61F 2/30744* (2013.01); *A61F 2/32* (2013.01); *A61F 2/34* (2013.01); *A61F 2/367* (2013.01); *A61F 2/3662* (2013.01); *A61F 2002/009* (2013.01); *A61F 2002/2821* (2013.01); *A61F 2002/305* (2013.01); *A61F 2002/30235* (2013.01); *A61F 2002/30322* (2013.01); *A61F 2002/30329* (2013.01); *A61F 2002/30354* (2013.01); *A61F 2002/30405* (2013.01); *A61F 2002/30438* (2013.01); *A61F 2002/30535* (2013.01); *A61F 2002/30589* (2013.01); *A61F 2002/30604* (2013.01); *A61F 2002/30668* (2013.01); *A61F 2002/30677* (2013.01); *A61F 2002/30718* (2013.01); *A61F 2002/30795* (2013.01); *A61F 2002/30932* (2013.01); *A61F 2002/368* (2013.01); *A61F 2002/3611* (2013.01); *A61F 2002/3625* (2013.01); *A61F 2002/3631* (2013.01); *A61F 2002/3692* (2013.01); *A61F 2002/482* (2013.01); *A61F 2220/0025* (2013.01); *A61F 2220/0033* (2013.01); *A61F 2220/0041* (2013.01); *A61F 2230/0069* (2013.01); *A61F 2250/0001* (2013.01); *A61F 2250/0026* (2013.01); *A61F 2250/0043* (2013.01); *A61F 2250/0058* (2013.01); *A61F 2310/00029* (2013.01); *A61F 2310/0052* (2013.01); *A61F 2310/00059* (2013.01); *A61F 2310/00065* (2013.01); *A61F 2310/00071* (2013.01); *A61F 2310/00077* (2013.01); *A61F 2310/00083* (2013.01); *A61F 2310/00107* (2013.01); *A61F 2310/00113* (2013.01); *A61F 2310/00149* (2013.01); *A61F 2310/00155* (2013.01); *A61F 2310/00395* (2013.01); *A61F 2310/00413* (2013.01); *A61F 2310/00449* (2013.01); *A61F 2310/00455* (2013.01); *A61F 2310/00461* (2013.01); *A61F 2310/00467* (2013.01); *A61F 2310/00473* (2013.01); *A61F 2310/00514* (2013.01); *A61F 2310/00562* (2013.01); *A61F 2310/00568* (2013.01); *A61L 2300/102* (2013.01); *A61L 2300/104* (2013.01); *A61L 2300/404* (2013.01); *A61L 2300/602* (2013.01); *A61L 2300/606* (2013.01); *A61L 2430/02* (2013.01); *A61N 1/205* (2013.01)

(56) References Cited

U.S. PATENT DOCUMENTS

| | | | |
|---|---|---|---|
| 4,025,619 A | 5/1977 | Perlman et al. | |
| 4,027,393 A | 6/1977 | Ellis | |
| 4,054,139 A | 10/1977 | Crossley | |
| 4,100,920 A | 7/1978 | Le Goaster | |
| 4,252,525 A | 2/1981 | Child | |
| 4,291,125 A | 9/1981 | Greatbatch | |
| 4,308,859 A | 1/1982 | Child | |
| 4,476,590 A | 10/1984 | Scales | |
| 4,569,673 A | 2/1986 | Tesi | |
| 4,615,705 A | 10/1986 | Scales et al. | |
| 5,100,671 A | 3/1992 | Maeda | |
| 5,322,520 A | 6/1994 | Milder | |
| 5,324,275 A | 6/1994 | Raad et al. | |
| 5,358,514 A | 10/1994 | Schulman | |
| 5,383,935 A | 1/1995 | Shirkhanzadeh | |
| 5,441,955 A | 8/1995 | Baker et al. | |
| 5,520,664 A | 5/1996 | Bricault | |
| 5,723,014 A | 3/1998 | Laurent et al. | |
| 5,725,817 A | 3/1998 | Milder et al. | |
| 5,741,224 A | 4/1998 | Milder et al. | |
| 5,759,564 A | 6/1998 | Milder et al. | |
| 5,814,091 A | 9/1998 | Dahlberg | |
| 5,814,094 A | 9/1998 | Becker | |
| 5,817,325 A | 10/1998 | Sawan et al. | |
| 5,984,905 A | 11/1999 | Dearnaley | |
| 6,034,295 A | 3/2000 | Rehberg | |
| 6,087,549 A | 7/2000 | Flick | |
| 6,120,502 A | 9/2000 | Michelson | |
| 6,120,520 A | 9/2000 | Saadat et al. | |
| 6,143,035 A | 11/2000 | McDowell | |
| 6,238,686 B1 | 5/2001 | Burrell | |
| 6,267,590 B1 | 7/2001 | Barry | |
| 6,393,323 B1 | 5/2002 | Sawan | |
| 6,500,165 B1 | 12/2002 | Frank | |
| 6,579,539 B2 | 6/2003 | Lawson | |
| 6,582,715 B1 | 6/2003 | Barry | |
| 6,610,096 B2 | 8/2003 | MacDonald | |
| 6,663,634 B2 | 12/2003 | Ahrens | |
| 6,731,897 B2 | 5/2004 | Nagano et al. | |
| 6,731,987 B1 * | 5/2004 | McAdams | A61N 1/0436 600/372 |
| 6,778,861 B1 | 8/2004 | Liebrecht | |
| 7,615,070 B2 | 11/2009 | Biscup | |
| 8,135,466 B2 | 3/2012 | Fuller et al. | |
| 8,609,036 B2 | 12/2013 | Fuller et al. | |
| 8,620,431 B2 | 12/2013 | Fuller et al. | |
| 9,008,770 B2 | 4/2015 | Fuller et al. | |
| 9,421,285 B2 | 8/2016 | Fuller et al. | |
| 9,561,294 B2 | 2/2017 | Fuller et al. | |

(56) References Cited

U.S. PATENT DOCUMENTS

| | | | |
|---|---|---|---|
| 9,561,295 | B2 | 2/2017 | Fuller et al. |
| 9,566,359 | B2 | 2/2017 | Fuller et al. |
| 2002/0055761 | A1 | 5/2002 | Mann et al. |
| 2004/0243130 | A1 | 12/2004 | Biscup |
| 2006/0004431 | A1 | 1/2006 | Fuller et al. |
| 2006/0265026 | A1 | 11/2006 | Madjar et al. |
| 2008/0199352 | A1 | 8/2008 | Fuller et al. |
| 2009/0259319 | A1 | 10/2009 | DiSilvestro et al. |
| 2010/0100188 | A1 | 4/2010 | Fuller et al. |
| 2010/0198357 | A1 | 8/2010 | Fuller et al. |

FOREIGN PATENT DOCUMENTS

| | | |
|---|---|---|
| JP | 2002-536048 A | 10/2002 |
| WO | WO 95/32673 | 12/1995 |
| WO | WO 97/38648 | 10/1997 |
| WO | WO 00/45724 | 8/2000 |
| WO | WO 2004/017738 A1 | 4/2004 |
| WO | WO 2007/005842 A2 | 1/2007 |
| WO | WO 2008/082586 | 7/2008 |

OTHER PUBLICATIONS

Berger, T.J. et al. "Antifungal Properties of Electrically Generated Metallic Ions", Antimicrobial Agents and Chemotherapy, Nov. 1976, vol. 10, No. 5, pp. 856-860.

Sudmann, Einar, et al., "Systemic and Local Silver Accumulation after Total Hip Replacement using Silver-Impregnated Bone Cement", Medical Progress Through Technology, 1994, pp. 179-31, 20(3-4).

Tozzi, Piergiorgio et al., "Silver-coated Prosthetic Heart Value: A Double-bladed Weapon", European Journal of Cardio-thoracic Surgery, 2001, pp. 729-731, No. 19.

MacKeen, Patricia C., et al. "Silver-coated Nylon Fiber as an Antibacterial Agent", Antimicrobial Agents and Chemotherapy, Jan. 1987, pp. 93-99, vol. 31, No. 1.

Deitch, Edwin A. et al, "Silver-Nylon: A New Antimicrobial Agent", Antimicrobial Agents and Chemotherapy, Mar. 1983, pp. 356-359, vol. 23, No. 3.

Becker, R. et al., "Treatment of Orthopaedic Infections with Electrically Generated Silver Ions", The Journal of Bone and Joint Surgery, Oct. 1978, pp. 871-881, vol. 60-A, No. 7.

Hall, R. et al. "Inhibitory and Cidal Antimicrobial Actions of Electrically Generated Silver Ions", J. Oral Maxillofac. Surg., Sep. 1987, pp. 779-784, vol. 45(9).

Straub, A.S., et al., "Phase 1 Evolution of a Local Delivery Device Releasing Silver Ions in Periodontal Pockets: SafetyPharmacokinetics and Bioavailability", Journal of Periodontal Research, 2001, pp. 187-193, 36.

Van Der Borden, A., et al., "Electric Current-Induced Detachment of *Staphylococcus epidermidis* Biofilms from Surgical Stainless Steel", Applied and Environmental Microbiology, Nov. 2004, pp. 6871-6874, vol. 70, No. 11.

Beal, Dr Charles D., "Silver Ion Therapy for HIV/AIDS and Septicemia", Copyright notice: "Copyright 1999, Life & Health Research Group".

Written opinion of the ISA issued in PCT/US2006/026000, dated Dec. 19, 2006.

International Search Report issued in PCT/US2006/026000, dated Dec. 19, 2006.

Int. prel. rpt. on pat. issued in PCT/US2006/026000, dated Jan. 9, 2008.

Written Opinion of the ISA in PCT/US2007/026379, dated Sep. 9, 2008.

International Search Report and Written Opinion issued in PCT/US2007/26379, dated Sep. 9, 2008.

Response to International Search Report and Written Opinion in PCT/US2007/026379, dated Jan. 8, 2009.

International Preliminary Report on Patentability issued in PCT/US2007/026379, dated Sep. 30, 2009.

First Official Notification by the Israeli Patent Office in Israeli Patent Application No. 188251, dated Jul. 21, 2010.

Israel Patent Application Serial No. 188251, Response to office action dated Jun. 21, 2010.

Office Action dated Nov. 13, 2011, by the Israel patent office in Patent Application Serial No. 188251.

English translation of a section of the Nov. 13, 2011 Israel office action that addresses rejections on the basis of prior art (paragraphs 3, 4 and 5).

Japan Patent Application Serial No. 2008-519693—Translation of first office action.

English translation of office action dated Apr. 27, 2011 by the Japanese patent office in Japan Patent Application Serial No. 2008-519693.

English translation of office action dated Jul. 2012 by the Japanese patent office in Japan Patent Application Serial No. 2008-519693.

Japanese language response, filed on Oct. 27, 2011 in Japan Patent Application Serial No. 2008-519693.

English translation of Japanese language response filed Oct. 27, 2011 and disclosed herein, filed in Japan Patent Application Serial No. 2008-519693.

Written Opinion issued by Intellectual Property Office in Singapore in Singapore Pat. App. No. 200718944-2.

Response to Written Opinion in Singapore in Singapore Pat. App. No. 200718944-2, dated Aug. 28, 2009.

Written Opinion issued by Intellectual Property Office in Singapore in Singapore Pat. App. No. 200718944-2 , dated Dec. 28, 2009.

Response to Written Opinion in Singapore Pat. App. No. 200718944-2, dated May 26, 2010.

Examination Report issued by the Intellectual Property Office in Singapore in Singapore Pat. App. No. 200718944-2, dated Sep. 16, 2010.

Singapore Patent Application Serial No. 200718944-2—Amendment prior to issuance—Mailed to IPO on Dec. 10, 2010.

Written Opinion issued by Intellectual Property Office in Singapore in Singapore Pat. App. No. 200718944-2, dated Mar. 2, 2009.

Application and file history for U.S. Appl. No. 12/005,649, filed Dec. 27, 2007, now U.S. Pat. No. 8,609,036 on Dec. 17, 2013, inventors Fuller et al.

Application and file history for U.S. Appl. No. 14/090,624, filed Nov. 26, 2016, now U.S. Pat. No. 9,561,624 on Feb. 7, 2017, inventors Fuller et al.

Application and file history for U.S. Appl. No. 14/103,238, filed Dec. 11, 2013, now U.S. Pat. No. 9,561,295 on Feb. 7, 2017, inventors Fuller et al.

Application and file history for U.S. Appl. No. 14/103,276, filed Dec. 11, 2013, now U.S. Pat. No. 9,566,359 on Feb. 14, 2017, inventors Fuller et al.

Application and filed history for U.S. Appl. No. 11/922,979, filed Mar. 6, 2009, now U.S. Pat. No. 8,135,466 on Mar. 13, 2012, inventors Fuller et al.

Application and file history for U.S. Appl. No. 11/172,138, filed Jun. 30, 2005, inventors Fuller et al.

Application and file history for U.S. Appl. No. 12/759,455, filed Apr. 13, 2010, inventors Fuller et al.

Application and file history for U.S. Appl. No. 13/417,269, filed Mar. 11, 2012, now U.S. Pat. No. 8,620,431 on Dec. 31, 2013, inventors Fuller et al.

Application and file history for U.S. Appl. No. 14/090,699, filed Nov. 26, 2013, now U.S. Pat. No. 9,008,770 on Apr. 14, 2015, inventors Fuller et al.

Application and file history for U.S. Appl. No. 14/644,497, filed Mar. 11, 2015, now U.S. Pat. No. 9,421,285 on Aug. 23, 2016, inventors Fuller et al.

\* cited by examiner

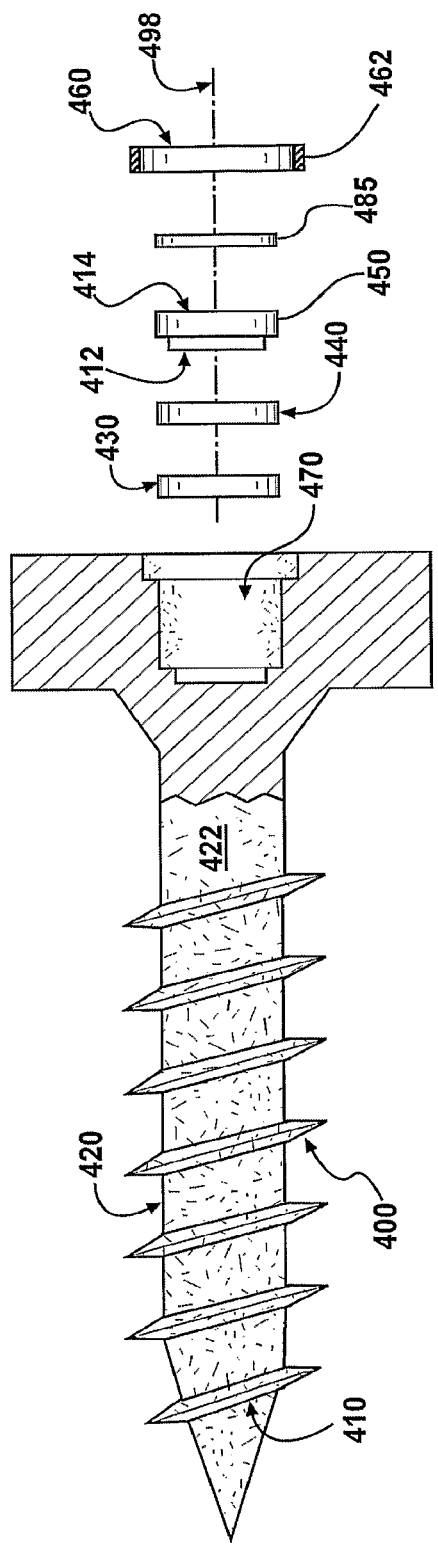
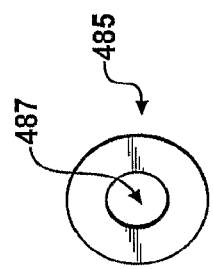
FIG - 4
FIG - 4A

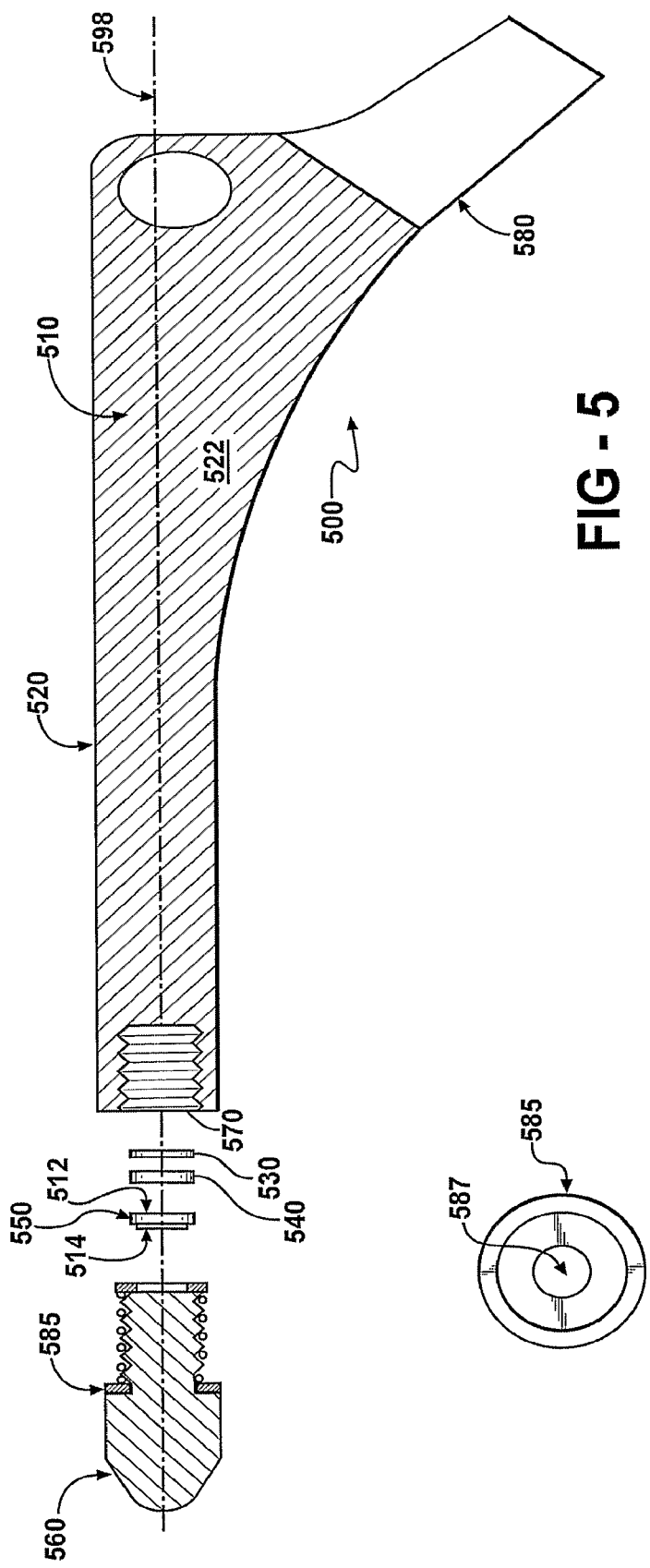

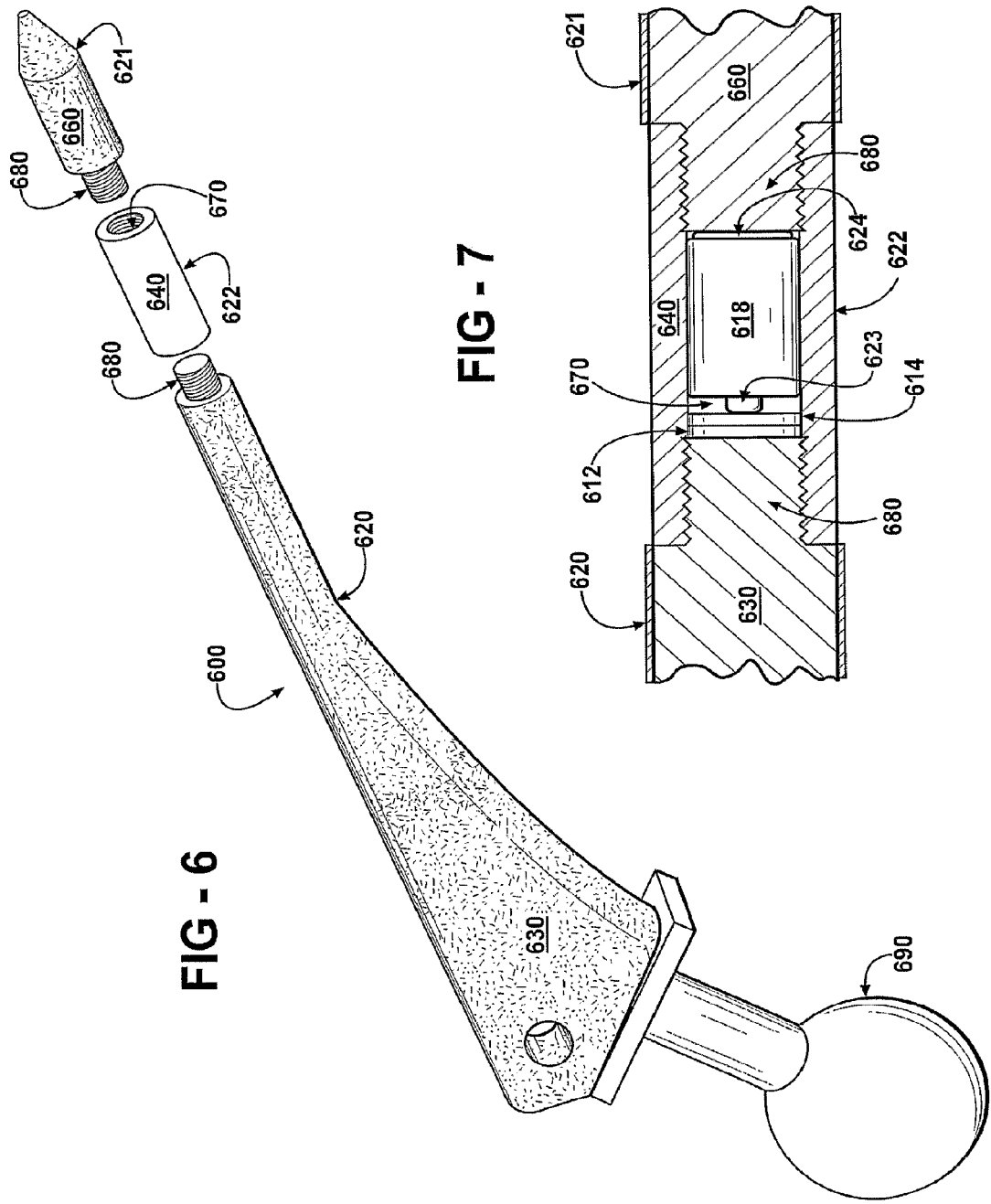

PROPHYLACTIC BACTERICIDAL MEDICAL DEVICE

REFERENCE TO RELATED APPLICATIONS

This application is a continuation of U.S. patent application Ser. No. 14/644,497, issued as U.S. Pat. No. 9,421,285 on Aug. 23, 2016, which is a continuation of U.S. patent application Ser. No. 14/090,699, issued as U.S. Pat. No. 9,008,770 on Apr. 14, 2015, which is a continuation of U.S. patent application Ser. No. 13/417,269, issued as U.S. Pat. No. 8,620,431 on Dec. 31, 2013, which is a continuation of U.S. patent application Ser. No. 11/922,979, issued as U.S. Pat. No. 8,135,466 on Mar. 13, 2012, which is a national stage entry of PCT/US2006/026000, filed Jun. 30, 2006, which is published, which is a continuation in part of U.S. patent application Ser. No. 11/172,138, filed Jun. 30, 2005, which is now abandoned and claims priority from U.S. Provisional Patent Application Ser. No. 60/708,320, filed Aug. 15, 2005, which is now abandoned, the entire content of each of which is incorporated herein by reference.

FIELD OF THE INVENTION

The invention relates to systems and methods for inhibition of microbial infection related to surgical implant devices. In particular, the invention relates to systems and methods for inhibition of microbial infection related to orthopedic implants.

BACKGROUND OF THE INVENTION

Joint degeneration is the leading chronic condition in the elderly; it affects one in every eight Americans and almost half the population over the age of 65. (Brooks, P. M, Med. J. Aust., 173:307-308, 2000) The most common form of joint degeneration is osteoarthritis. Osteoarthritis weakens and breaks down cartilage and bone, causing pain as bones rub together. Eventually the constant rubbing of the bony surfaces destroys the surfaces that are rubbing against one another leading to rough, painful movement. Total joint replacement, or arthroplasty, represents a significant advance in the treatment of painful and disabling joint pathologies. Arthroplasty can be performed on almost any joint of the body including the hip, knee, ankle, foot, shoulder, elbow, wrist, and fingers. Total joint replacement: whether hip, knee, ankle, foot, shoulder, elbow, wrist, and fingers or other, is typically done as a final stage treatment for a patient who suffers from some form of joint degeneration.

In its early stages, many people manage arthritis pain conservatively by using anti-inflammatory medicines, weight reduction, lifestyle modification, physiotherapy, or occupational therapy. However, as the disease progresses the pain intensifies. When the pain gets to the point where everyday, normal activities such as putting on shoes and socks or walking up stairs become too painful, total joint replacement surgery is an attractive option to restore movement and independence, and to dramatically reduce pain.

Although joint replacement is a relatively large field within orthopedics, the number of fracture fixation devices utilized around the world far outranks the number of artificial joints. Fracture fixation is growing daily as the number of fractures associated with trauma accidents is increasing. Fixation devices can be internal or external in nature and include devices such as a plate, wire, screw, pin, rod, nail or staple, which aid in maintaining fracture fragments in proper position during healing. Such devices are usually inserted after open reduction of the fracture and will remain for the entirety of the healing process, often becoming a permanent structure within the body.

Joint replacement surgery began in the early 1950's, and its frequency has grown as surgical techniques and medical care associated with surgery improves. In the late 1980's between 500,000 and 1 million total hip replacements were performed per year, while in 2004 it is estimated that approximately 600,000 joint prosthesis and 2,000,000 fracture-fixation devices will be inserted into patients in the United States.

Unfortunately, as the number of implant surgeries increases, the number of associated infections also increases. Any person who has an implant is at risk for developing an infection associated with the device. It is estimated that 2 percent of joint prostheses and 5 percent of fixation devices will become infected. Taking 3 percent as an average estimate of infected implants, as many as 30 million incidents of infection may occur.

The effects of implant infection are expensive as well as a danger to the health and well-being of the affected individual. For example, infection results in direct medical and surgical costs and additionally may cause patient pain, suffering, lost wages, lost work and decreased productivity. On average an infected hip prosthesis patient spends six times the number of days in the hospital when compared to the non-infected prosthetic hip patient. In 1991, the total cost of an infected patient, both in hospital and as an outpatient, was $45,000 as compared to the total cost of $8,600 associated with a non-infected patient. (Bengston, S., Ann. Med., 25:523-529, 1993)

Joint replacement implants and fixation devices include a variety of materials foreign to the human body, such as metals, plastics, and polymeric substances, all of which have the potential to serve as substrates for attachment and growth of microorganisms.

In particular, certain microorganisms may exude a glycocalyx layer that protects certain bacteria from phagocytic engulfment by white blood cells in the body. The glycocalyx also enables some bacteria to adhere to environmental surfaces (metals, plastics, root hairs, teeth, etc.), colonize, and resist flushing.

Once microorganisms colonize an implant, it is often very difficult to eradicate or even inhibit the infection. For example, systemic administration of antibiotics is often ineffective due to limited blood supply to the areas of the implant. Additionally, many bacterial species today are resistant to antibiotics.

Where infection cannot be inhibited it may spread and become even more serious, as in patients who have an infection within the bone, osteomyelitis. Such patients often must undergo a difficult and costly treatment involving extended hospitalization, joint debridement, aggressive antimicrobial therapy, total joint removal followed by total joint replacement and possible amputation if the infection can not be eliminated.

Since implantation of an orthopedic implant device, such as a joint replacement prosthesis or fixation device, is quite common and associated infection frequent, there is a continuing need for new approaches to inhibition of infection. In particular, it would be very desirable for both the physician as well as the patient to be able to treat a prosthetic osteomyelitic infection without the removal of an implant.

Further, economical and safe apparatus and methods of inhibiting implant associated infections are needed.

SUMMARY OF THE INVENTION

A medical implant system includes an implant body made of a biocompatible material. The implant body has an external surface and a metal component containing an antimicrobial metal is disposed on the external surface of the implant body. A medical implant system according to the present invention includes a power source having a first terminal and a second terminal and further includes an insulator placed in a current path between the first terminal of the power source and the second terminal of the power source preventing current flowing from the first terminal from reaching the second terminal without completing a circuit including a conductive body tissue or fluid adjacent to the external surface of the implant system when implanted.

A medical implant system according to the present invention may be configured as any of various types of implant. Optionally, an implant body is a joint replacement prosthetic implant. In a further option an implant body is a part of a joint replacement prosthetic implant. An implant body may also be an orthopedic fixation device, an orthopedic spacer, or a combination of a joint replacement prosthetic implant, an orthopedic fixation device, or an orthopedic spacer.

More than one implant body may be included as part of an inventive system. In addition, more than one power source may be provided, for example, where more than one implant body is included.

In a highly preferred embodiment, a medical implant system is provided having an implant body which includes a first element having a first external surface and a second element having a second external surface, as well as a first metal component containing an antimicrobial metal which is disposed on at least the first external surface of the implant body. A power source having a first terminal and a second terminal is included in an inventive implant and the first terminal is in electrical communication with the first metal component. The second terminal is in electrical communication with the second external surface. An insulator is placed in a current path between the first terminal of the power source and the second terminal of the power source preventing current flowing from the first terminal from reaching the second terminal without completing a circuit including a conductive body tissue or fluid adjacent to the external surface of the implant system when implanted.

In a preferred option, a second metal component containing an antimicrobial metal is disposed on the second external surface, and the second terminal is in electrical communication with the second metal component. In such a configuration, the insulator insulates the first metal component from the second metal component.

In one embodiment, an internal cavity having a wall and an opening is included in the implant body and a cap is provided to close the opening of the internal cavity. A power source is positioned in the internal cavity.

In one embodiment of the present invention, a portion of the cap in contact with the wall of an internal cavity includes an electrically insulating material preventing current flowing from the first terminal of the power source from reaching the second terminal of the power source without completing a circuit including a conductive body tissue or fluid adjacent to the external surface of the implant system when implanted. For example, at least a portion of the cap in contact with the wall of an internal cavity may be made of an insulating material or may have a coating of an insulating material, forming an insulating region. The insulating region may extend a distance from the region of contact with the wall. However, it is appreciated that a cap optionally provides a current path from an external surface to a power source terminal, and therefore, the cap may provide such a current path in regions of the cap away from contact with the wall.

A medical implant system is provided according to an embodiment of the present invention which includes an implant body having a main body portion having a first external surface and a cap portion having a second external surface. An antimicrobial metal-containing coating, such as a silver-containing coating, is disposed on the first external surface of the main body portion. A power source having a first terminal and a second terminal is provided as part of an inventive system, the first terminal of the power source is in electrical communication with the silver-containing coating and the second terminal is in electrical communication with the second external surface. An insulator is placed in a current path between the first terminal of the power source and the second terminal of the power source preventing current flowing from the first terminal from reaching the second terminal without completing a circuit including a conductive body tissue or fluid adjacent to the external surface of the implant system when implanted. An internal cavity is present in the implant body and the power source is disposed therein. The internal cavity and power source may be positioned at any convenient position. In a preferred embodiment, the internal cavity is in the main body portion. Alternatively, an intermediate portion having an internal cavity may be provided and attached to the main body portion and the cap.

In a specific embodiment, a cap is provided which includes a protruding portion, the internal cavity comprises a threaded surface and the insulator comprises a screw thread insert, and wherein the protruding portion of the cap interacts with the screw thread insert to form a male connector for reciprocal interaction of the threaded surface of the internal cavity and the male connector.

A medical implant system is provided in the form of an orthopedic fixation device in one embodiment. An inventive device includes a support structure for supporting at least two orthopedic fixators. The support structure is adapted to secure the at least two orthopedic fixators to the support. A first orthopedic fixator supported by the support structure has a first external surface and a second orthopedic fixator supported by the support structure has a second external surface. A first metal component containing an antimicrobial metal is disposed on the first external surface of the first fixator. A power source having a first terminal and a second terminal is included and the first terminal is in electrical communication with the first metal component. An insulator is disposed on the support structure in a current path between the first terminal of the power source and the second terminal of the power source preventing current flowing from the first terminal from reaching the second terminal without completing a circuit including a conductive body tissue or fluid adjacent to the external surface of the first fixator when implanted.

In a preferred option, the implant is adapted to be disposed totally within a human body when in use as an implant. Thus, for example, no wires or other conductive elements protrude from the body of an individual having an inventive implant. In the case of an orthopedic fixation device, certain embodiments include a support structure, power source and/or a portion of a fixator present outside the body of a patient when at least a portion of the fixator is implanted.

Also optionally, a current conductor, such as a metal component, is disposed on a portion of the internal cavity wall, preferably such that the portion of the metal component in the cavity is continuous with the portion of the metal component disposed on the external surface of the implant body. Also preferably, the metal component in the cavity has the same composition as the metal component on the external surface. Optionally, the form of the metal component in the cavity is the same or different compared to the form of the metal component on the external surface. For example, a wire or metal ribbon may be attached to the metal component on the external surface and to the cavity wall. In one embodiment, the metal component in the cavity is in contact with a terminal of a power source disposed therein.

In a preferred option, the metal component includes a transition metal and/or a metal found in columns 10-14 of the Periodic Table of Elements, selected from gold, zinc, cobalt, nickel, platinum, palladium, manganese, and chromium. In a preferred embodiment of an inventive implant system, a metal component includes an antimicrobial metal which is silver; copper, both silver and copper; both silver and cadmium; both copper and cadmium; or a combination of silver, copper and cadmium. In further embodiments, the metal component includes a metal selected from the group consisting of: gold, zinc, cobalt, nickel, platinum, palladium, manganese, chromium; or a combination of these.

In a further preferred option, the metal component is more electrically conductive than the biocompatible material of the implant body.

One form of a metal component is a coating disposed on the external surface of the implant body. Such a metal coating ranges in thickness between $1 \times 10^{-9}$-$5 \times 10^{-3}$ meters, inclusive.

Optionally, a metal coating disposed on a portion of the external surface of the implant body covers a portion of the external surface ranging from 1-100% of the total external surface of the implant body, excluding any portion of the external surface occupied by the insulator. Further optionally, the metal coating disposed on a portion of the external surface of the implant body covers a portion of the external surface ranging from 50-99 percent of the external surface of the implant body. Preferred is a configuration in which the metal coating is disposed as a single region of continuous coating on the external surface.

In one embodiment of an inventive medical implant system the implant body includes an articular surface which does not include a metal component such as a metal coating.

In another option, a metal component is provided in the form of a wire, ribbon, or foil disposed on the external surface.

An inventive system may be configured such that the power source is continuously powering a current conducted to the metal component for release of metal ions. Alternatively, a system includes a switch for powering the current on or off. In a further embodiment, the current is modulated by circuitry adapted to control the current so as to increase or decrease the amount of current flowing and the amount of metal ions released. Thus, a resistor in electrical communication with the power source is optionally included. In a preferred embodiment, the resistor and power source are positioned in an internal cavity of the implant body. Optionally, a switch in electrical communication with the power source is included to control the power source. Further optionally, a controller in signal communication with the switch is provided. Such a controller is operated to send a signal to a system component adapted to receive the signal and to control the switch. Preferably, a controller is external to an individual having the implant, such that activation of the switch may be performed by a doctor, technician or by the patient.

Also described is a method for inhibiting microbial infection associated with an orthopedic implant, which includes providing an inventive system and delivering a current to a metal component disposed on an external surface of an implant body, the implant body located in a human body at a site of potential infection. Delivery of current to the metal component is associated with antimicrobial action such as release of metal ions toxic to an infectious microbe at the site of potential infection, such that microbial infection is inhibited.

In one embodiment of an inventive method, the infectious microbe is a Gram positive bacterium and the metal component comprises an antimicrobial metal selected from the group consisting of silver, copper; both silver and copper; both silver and cadmium; both copper and cadmium; and a combination of silver, copper and cadmium. In additional options, the infectious microbe is a Gram negative bacterium and the metal component comprises an antimicrobial metal selected from the group consisting of: copper; and both copper and cadmium. In further embodiments, the infectious microbe is a fungus and the metal component comprises an antimicrobial metal selected from the group consisting of: silver; and both silver and copper.

BRIEF DESCRIPTION OF THE DRAWINGS

FIG. 4 is a line drawing of an inventive bone screw implant system including an insulator;

FIG. 4A is a line drawing of a view of an insulator;

FIG. 5 is a line drawing of an inventive hip implant system including an insulator;

FIG. 5A is a line drawing of a view of an insulator;

FIG. 6 is a line drawing of an apparatus according to an embodiment of the invention in the form of a hip joint implant showing an exterior view of the implant;

FIG. 7 is a line drawing of an apparatus according to an embodiment of the invention in the form of a hip joint implant showing an interior view of the implant;

DETAILED DESCRIPTION OF THE INVENTION

Figure 1:
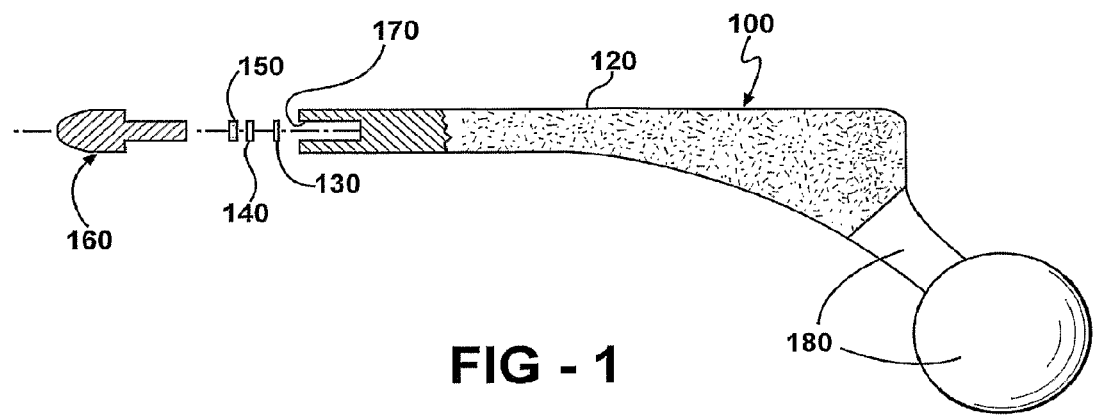
FIG. 1 is a line drawing of an apparatus according to an embodiment of the invention in the form of a hip joint implant showing a portion of the exterior of the implant and a cut away portion.

The present invention provides methods and apparatus for prevention and inhibition of implant-associated infection.

A medical implant system is provided which allows for release of microbe-inhibiting metal ions in the vicinity of a temporary or permanent surgically implanted device. In particular, metal ions are released from a metal component of an implant by application of an electrical current to the metal component. A power source for producing the electrical current is provided which may be external to the implant, or preferably, contained within the implant.

A medical implant system is provided which includes an implant body made of a biocompatible material. A metal component is disposed on the external surface of the implant body and a power source is included to power delivery of an electrical current to the metal component. The electrical current is delivered to the metal component via an electrical conduit. In a preferred embodiment, the metal component is different than the biocompatible material. Thus, where the biocompatible material is a metal, the metal component differs in composition from the biocompatible material. For instance, preferably, the metal component has a higher conductivity than the biocompatible material.

Highly preferred is a medical implant system which includes an implant body having a first element having a first external surface and a second element having a second external surface, as well as a first metal component containing an antimicrobial metal which is disposed on at least the first external surface of the implant body. A power source having a first terminal and a second terminal is included in an inventive implant and the first terminal is in electrical communication with the first metal component. The second terminal is in electrical communication with the second external surface. An insulator is placed in a current path between the first terminal of the power source and the second terminal of the power source preventing current flowing from the first terminal from reaching the second terminal without completing a circuit including a conductive body tissue or fluid adjacent to the external surface of the implant system when implanted.

In a preferred option, a second metal component containing an antimicrobial metal is disposed on the second external surface, and the second terminal is in electrical communication with the second metal component. In such a configuration, the insulator insulates the first metal component from the second metal component.

The term "implant body" as used herein refers to an orthopedic implant for replacement or repair of a component of the musculoskeletal system. For example, an orthopedic implant includes a joint replacement prosthetic implant for joint replacement or repair. Prosthetic implants include those for replacement or repair of any joint illustratively including a knee, a hip, an ankle, a shoulder, a wrist, and a finger or toe joint among others. Further, an orthopedic implant is an orthopedic fixation device used in replacement or repair of a component of the musculoskeletal system, such as a plate, wire, screw, pin, rod, nail or staple. An orthopedic fixation device may include multiple fixators such as a plate, wire, screw, pin, rod, nail or staple. In one preferred embodiment, an implant body is an implant body which is wholly contained within a patient's body when in use for the purpose of the implant.

An implant body may include two or more separate or separable elements which are implanted or partially implanted together, illustratively including a main implant body, a cap and two or more fixators. Thus, in certain preferred embodiments, an inventive implant system includes at least a first element and a second element of an implant body.

In additional preferred embodiments, an implant body is partially external, for example, an external fixation device. An external fixation device includes one or more fixators which are partially external to the patient's body in use. An external fixation device may further include a support for the one or more fixators.

The term "biocompatible material" as used herein refers to a material which is relatively inert in use following surgical placement into an individual such that adverse reactions such as inflammation and rejection are rare. The biocompatible material is sufficiently strong and durable to allow the implant to perform its intended function, such as joint replacement or fixation. Exemplary biocompatible materials include metal materials such as surgical stainless steel, titanium, and titanium alloys; ceramics; plastics; and combinations of these.

The metal component includes a metal which inhibits infection by microbes, such as bacteria, protozoa, viruses, and fungi. Such antimicrobial metals include transition metals and metals in columns 10-14 of the periodic table. Such metals illustratively include silver, gold, zinc, copper, cadmium, cobalt, nickel, platinum, palladium, manganese, and chromium. In certain embodiments, lead and/or mercury may be included in amounts not significantly toxic to the patient. Highly preferred is a metal component containing an antimicrobial metal which generates metal ions in response to application of current to the metal component as described herein.

A metal component contains an amount of an antimicrobial metal, the amount in the range of 1%-100% by weight of the total composition of the metal component. In general, a metal component included in an inventive implant system contains an amount of an antimicrobial metal in the range of about 1 nanogram to about 1 kilogram. A metal component preferably contains at least 50 percent by weight of an antimicrobial metal, further preferably contains at least 75 percent by weight of an antimicrobial metal and still further preferably contains at least 95 percent by weight of an antimicrobial metal. In another preferred embodiment, the metal component is substantially all antimicrobial metal. In particular, the metal component is capable of releasing a metal ion when an electrical current is applied to the metal component.

Materials other than an antimicrobial metal may also be included in a metal component. For instance, a metal component may further include metals which are non-antimicrobial in one configuration according to the invention, for instance to provide structural support and lower cost of the metal component. In an alternative embodiment, a non-metal constituent is included in the metal component, for instance to provide structural support and lower cost of the metal component. Exemplary non-metal constituents include such substances as inorganic and organic polymers, and biodegradable materials. A non-metal constituent or non-antimicrobial metal included in a metal component is biocompatible. Preferably, the metal component is electrically conductive.

A metal component may be provided in any of various forms, illustratively including, a substantially pure metal, an alloy, a composite, a mixture, and a metal colloid. Thus, in one embodiment, a metal component is a substance doped with an antimicrobial metal. For instance, in a particular example, a stainless steel and/or titanium alloy including an antimicrobial metal may be included in a metal component.

The antimicrobial properties of silver are particularly well-characterized and a metal component preferably contains an amount of silver, the amount in the range of 1 percent-100 percent by weight of the total composition of the metal component. A metal component preferably contains at least 50 percent by weight of silver, further preferably contains at least 75 percent by weight silver and still further preferably contains at least 95 percent by weight silver. In another preferred embodiment, the metal component is substantially all silver.

Copper is also a preferred metal included in a metal component and a metal component preferably contains an amount of copper in the range of 1%-100% by weight of the total composition of the metal component. In one embodiment, at least 50% by weight copper is included, further preferably a metal component contains at least 75% by weight copper and still further preferably contains at least 95% by weight copper. In another preferred embodiment, the metal component is substantially all copper. In particular, the metal component is capable of releasing a metal ion when an electrical current is applied to the metal component.

A combination of metals is also contemplated as included in a metal component. In some instances, certain metals may be more effective at inhibiting growth and/or killing particular species or types of bacteria. For example, particular metals are more effective at inhibiting growth and/or killing Gram positive bacteria, while other metals are more effective against Gram negative bacteria as exemplified in the Examples described herein.

In a particular embodiment, both silver and copper are included in a metal component. A combination of silver and copper may provide a synergistic antimicrobial effect. For instance, a lesser amount of each individual metal may be needed when a combination is used. Additionally, a shorter treatment time may be indicated where a synergistic effect is observed. The ratio of copper to silver in a metal component may range from 1000:1-1:1000. In one embodiment, a metal component preferably contains an amount of a copper/silver combination in the range of 1-100 percent by weight of the total composition of the metal component. In one embodiment, at least 50 percent by weight of a copper/silver combination is included, further preferably a metal component contains at least 75 percent by weight of a copper/silver combination and still further preferably contains at least 95 percent by weight of a copper and silver in combination. In another preferred embodiment, the metal component is substantially all copper and silver.

In a further preferred embodiment, a metal which has antimicrobial properties but which does not have increased antimicrobial properties when an electrical current is applied to the metal is included in a metal component. For example, cadmium has antimicrobial properties effective against a wide range of microbes, as described in the Examples, and which are not increased by application of an electrical current. Such a metal is optionally included in a metal component along with one or more metals capable of releasing a metal ion when an electrical current is applied to the metal component. In particularly preferred embodiments, cadmium and silver, cadmium and copper, or cadmium, silver and copper are included in a metal component. The ratio of one or more metals capable of releasing a metal ion when an electrical current is applied to the metal component to one or more metals whose antimicrobial activity is not increased when an electrical current is applied in a metal component may range from about 1000:1-1:1000. In one embodiment, a metal component preferably contains an amount of a copper and/or silver and an amount of cadmium such that the ratio of copper and/or silver to cadmium is in the range of about 1000:1-1:1000. A combination of silver and/or copper and cadmium in a metal component is in an amount in the range of about 1-100 percent by weight of the total composition of the metal component. In one embodiment, at least 50 percent by weight of a copper and/or silver and cadmium combination is included, further preferably a metal component contains at least 75 percent by weight of a copper and/or silver and cadmium combination and still further preferably contains at least 95 percent by weight of copper and/or silver and cadmium in combination. In another preferred embodiment, the metal component is substantially all copper and/or silver and cadmium. These and other combinations of antimicrobial metals in a metal component allow for tailoring an implant to a specific therapeutic situation.

In a preferred embodiment, the metal component is in the form of a coating disposed on the external surface of the implant body. The coating can be applied by any of various methods illustratively including dunk coating, thin film deposition, vapor deposition, and electroplating. The metal component in the form of a coating ranges in thickness between $1 \times 10^{-9}$-$5 \times 10^{-3}$ meters, inclusive, preferably $1 \times 10^{-7}$-$4 \times 10^{-3}$ meters, inclusive, and more preferably between $0.5 \times 10^{-6}$-$5 \times 10^{-4}$ meters in thickness.

In an example including a silver coating metal component, the total amount of silver used during the coating process ranges between about 1 nanogram in weight and about 100 grams in weight. Such a coating is at least 1 nanogram in weight in order for enough silver material to be present for the ionization to occur. The total weight of silver typically does not exceed about 100 grams in order to maintain a nontoxic state for the patient. However, both the lower and higher ends of this range may depend on the size and configuration of a particular implant and the localization of the metal component in relation to the implant body and are not intended to be limited to this range.

In an embodiment including a metal coating disposed on the external surface of the implant body, a metal coating is preferably disposed on at least 50 percent of the external surface of the implant body, and more preferably a coating is disposed on at least 75 percent of the external surface of the implant body. In an embodiment including a metal coating disposed on the external surface of the implant body, the coating is optionally disposed on substantially all of the external surface of the implant body. In a further option, the implant body is coated with the metal coating on substantially all of the external surface excluding one or more articular wear surfaces. An "articular wear surface" is a portion of an implant body which is exposed to wear during normal use when implanted. For example, a hip joint implant includes articular wear surfaces at the interface of the "ball" and "socket" components of the joint prosthesis, that is, at the acetabular surfaces. Where the implant body is a fixation device, it is preferred that the coating is present on at least 50 percent of the external surface of the implant body, and more preferably on at least 75 percent of the external surface of the implant body, and further preferably on substantially all of the external surface of the implant body, including threads where the device is a bone screw.

A coating may be disposed on a surface of an implant in a patterned fashion. For example, interlocking stripes of a metal component and an insulator may be arranged on a surface of an implant. Such a pattern is preferably designed to inhibit microbes around the entire perimeter of an implant. Thus, the distance between discontinuous regions of a coating is selected to account for the diffusion distance of ions generated from an antibacterial coating in response to an applied electrical current. Typically, ions diffuse a distance in the range of about 1-10 millimeters.

It is appreciated that, in the context of preferred embodiments of an implant system according to the present invention including at least two elements of an implant body, each element having a metal component, wherein the metal components are electrically isolated by an insulator, that each element optionally includes a metal component in the form of a metal-containing coating. In this context, the metal-containing coating on the one or more elements of the implant body is preferably present on at least 50 percent of the external surface of one or both elements of the implant body. More preferably the metal-containing coating on the one or more elements of the implant body is preferably present on at least 75 percent of the external surface of one or both elements of the implant body, and further preferably the metal-containing coating on the one or more elements of the implant body is preferably present on substantially all of the external surface of the one or more elements of the implant body, including threads where the device is a bone screw. However, an insulator disposed in a current path between the metal containing coating on the surface of the one or more elements electrically insulates one element from another and thus does not include a metal-containing coating in electrical communication with a metal-containing component on the one or more elements of the implant body.

A metal coating on an element of an implant body is preferably disposed on the external surface as a single continuous expanse of the coating material.

Optionally, the metal component is in the form of a wire, ribbon, or foil disposed on the external surface of an implant body. Such a metal component may be attached to the implant body by welding, by an adhesive, or the like.

In another embodiment, the implant body may include an antimicrobial metal such that the implant body or portion thereof is the metal component. A second metal component may be further included in contact with such an implant body. Thus, for example, an implant body or portion thereof may include an alloy of stainless steel and an antimicrobial metal, and/or an alloy of titanium and an antimicrobial metal. A commercial example of such a material is stainless steel grade 30430 which includes 3% copper.

In a further embodiment, an implant body made of a material including an antimicrobial metal may be formulated such that the antimicrobial metal is distributed non-uniformly throughout the implant body. For instance, the antimicrobial metal may be localized such that a greater proportion of the antimicrobial metal is found at or near one or more surfaces of the implant body.

In order to deliver an electrical current to the metal component and release antimicrobial metal ions, a power source is included in an inventive system. A power source may be any of various power sources such as a battery, capacitor, or connection to external AC. Such power sources are known in the art.

In one embodiment of an inventive system, a power source is implanted in the body of an individual receiving a joint prosthesis. An implant power source in such an embodiment is self-contained, that is, requiring no connection to external power. Illustrative examples include an electrochemical cell such as a battery and a capacitor. In a preferred embodiment, the implant body has an internal cavity housing the power source and, optionally, other components of the system, including circuitry adapted to modulate a current from the power source.

An internal cavity in an implant body includes a wall defining the cavity and an opening for insertion of a power source and, optionally, other components of the system.

In general, a preferred power source housed in an implant body cavity is lightweight and sized to fit in the cavity. In addition, a power source housed in an implant body cavity is capable of producing electrical currents in the range of 0.1-200 microamps. A power source housed in an implant cavity may be selected according to the requirements of a patient. For example, a temporary implant may not require a power source having as long a life expectancy as a permanent implant.

In a further embodiment, circuitry adapted to modulate an electrical current is included in an inventive system. Metal ions can be mobilized in greater quantities by increasing the current that is applied to the implant. If the current is increased a greater concentration of metal ions, preferably silver ions, will be provided near the surface of the implant. The greater concentration of silver ions will create a greater diffusion constant and provide for a greater distance of penetration by the ions. Similarly, current may be modulated to decrease ion release as desired, such as where no infection is believed to be present.

For example, a resistor, a switch, a signal receiver, a relay, a signal transmitter, transformer, a sensor, or a combination of these or other such components and connectors may be included, optionally configured as a circuit board arrangement. In a preferred embodiment, all or part of the circuitry adapted to modulate an electrical current included in an inventive system is housed in a cavity in the implant body of an orthopedic implant.

Thus, optionally, the internal cavity also contains a resistor for modulation of the current. For example, a resistor in series with a battery allows use of a larger size battery with a greater lifetime. The resistor in series can be used to reduce current flow to a desired level.

Once a power source capable of producing the required current and of the appropriate size is determined, a resistance can be calculated by using the equation; $V=I*R$, where V is the voltage of the battery that has been selected, I is the current, 1 microampere, and R is the resistance that will allow for the current to flow from the determined battery. This resistor then can be placed in series with the power source to yield the required current. A resistor is selected with reference to other considerations as well, including for example, the desired lifetime of the power source, the desired voltage and/or current. It is noted that neither the current nor the voltage delivered from a power source will be altered by the size of the implant.

In a specific example, a surface mounted chip resistor will satisfy the requirements of the resistor for use in this application. Surface mounted chip resistors come in a variety of resistances, ranging form 1 ohms up to 51 mega-ohms. Surface mounted chip resistors are manufactured in a variety of sizes which will meet the size constraints. For example, the Ohmite, thick film high voltage SMD chip, series MMC08 will easily fit within the shaft of the redesigned hip implant. The MMCO8 has dimensions of over all length of 2.0 millimeters and over all width of 1.25 millimeters. This particular resistor is manufactured in resistance between 100 ohms and 51 mega-ohms.

An inventive implant system may be configured such that a desired amount of an antimicrobial metal ion is released over a specified period of time so as to optimize the inhibitory effects on undesirable microbes and minimize any unwanted side effects. In one embodiment, an inventive implant system is configured such that an included power source is in continuous operation and metal ions are released continuously.

In a preferred option, a switch is included in an inventive system to control current to flow from the power source to the metal component. A switch allows antimicrobial ions to be released during specified periods of time by controlling current flow. For example, the switch is turned on to activate current and release antimicrobial ions at regular intervals, such as once a week or once a month, for a time following implantation in order to prevent infection. Further, where an infection is detected or suspected, the switch is activated to allow current flow and release of metal ions to combat the infection. An included switch is capable of withstanding the current and the voltage transferred across it. It is appreciated that all components included in an inventive implant system are selected to withstand use and the environment when in situ over a desired period of time.

A switch is optionally and preferably controlled by a controller external to the body of the individual having an implanted prosthesis. An external controller may emit a signal operative to control a switch. In one example, a magnetically controlled switch, such as a reed switch is used. Magnetically based switches that are externally controlled by a controller are currently manufactured and are available from commercial sources. Such switches are controlled by a controller including a magnet which is placed in proximity to the switch in order to turn the switch on or off. For example, a magnet may be positioned in the vicinity of a patient's hip in order to activate a magnetically controlled switch in an internal cavity of a hip prosthesis implant. Thus, the switch is in signal communication with the controller.

Optionally, a transmitter is included in an inventive system which is in signal communication with receiver circuitry adapted to operate a switch and modulate current flow. Preferably the transmitter is activated external to the body of an individual having an implanted prosthesis as described herein. For example, a radio frequency transmitter may be used to transmit a radio frequency signal to receiver circuitry in the internal cavity of the implant body adapted to operate a switch and modulate current flow.

In a further embodiment, microchip circuitry, programmed to modulate current flow is included in an inventive system. Preferably, the microchip circuitry is included in a cavity of an inventive implant body. In a further embodiment, such microchip circuitry may be implanted at a second location in the implant patient, such as just under the skin, to remotely control the current flow.

A sensor may be included to sense microbial growth, such as bacterial growth, on an external surface of an implant body, or elsewhere on the implant. Such a sensor may communicate a signal indicating bacterial growth to circuitry adapted to activate a switch, stimulating release of metal ions and inhibiting the microbes.

Preferably, the implant body having a power source in an internal cavity is adapted to be disposed totally within a human body when in use. Thus, the implant body preferably has substantially the same dimensions and shape of a conventional implant body.

In a preferred option, a portion of the metal component is disposed in the internal cavity. For example, in a preferred option, a metal coating is present on a portion of the wall of the internal cavity. Such a metal coating is preferably continuous with a metal component, such as a coating, disposed on the external surface of the implant body. Optionally, and preferably, a metal component present in the internal cavity is in electrical contact with one terminal of a power source present in the cavity. A metal component present in the cavity may also be in the form of a wire, ribbon, or foil. Preferably the metal component in the cavity is in the same form as the metal component present on the external surface of the implant body and is continuous therewith.

In a preferred option, a metal component disposed on the external surface and/or internal cavity wall is more electrically conductive than the biocompatible material of which the implant body is made.

The internal cavity has an opening which can be closed using a cap which may be attached to the implant body, such as by a hinge, or completely detachable.

A conduit for conduction of an electrical current from the power source is included in an inventive system. In one embodiment, the conduit is the biocompatible material of the implant body.

In a further embodiment, a power source is external to the body of the individual having the implanted prosthesis and the conduit traverses the skin of the individual, connecting the metal component disposed on the implant body with the external power source.

FIG. 1 illustrates an exemplary embodiment of an inventive apparatus 100 in a partial external, partial cut away view. A drawing illustrating a prophylactic bactericidal hip implant is shown having a metal component in the form of a metal-containing coating, such as a silver coating, depicted as stippling, on the external surface 120. An internal cavity 170 is shown in cut away sectional view, shown as the stripe marked region. This cavity allows for the internal placement of the battery, switch and resistor components. A switch 130, resistor 140 and battery 150 are shown, which are contained in the cavity. Although the resistor and switch are shown in particular order with respect to the battery and current path, these components may be placed elsewhere in the current path and in different respective order in this and other embodiments. The remaining end of the original shaft has been machined to form a cap 160 so that the cap 160 is disposed so as to form a cover for cavity 170 after assembly of the internal components in the cavity. In a particular embodiment, the cap forms a hermetic seal for the cavity such that components internal to the cavity are protected from the external environment and, in addition, the patient's body is protected from exposure to the components in the cavity. In this example, no coating is present on surfaces tending to wear due to interaction with other implant parts or natural elements of the body, e.g. articular surfaces, as shown without stippling or stripe marks at 180.

Figure 1A:
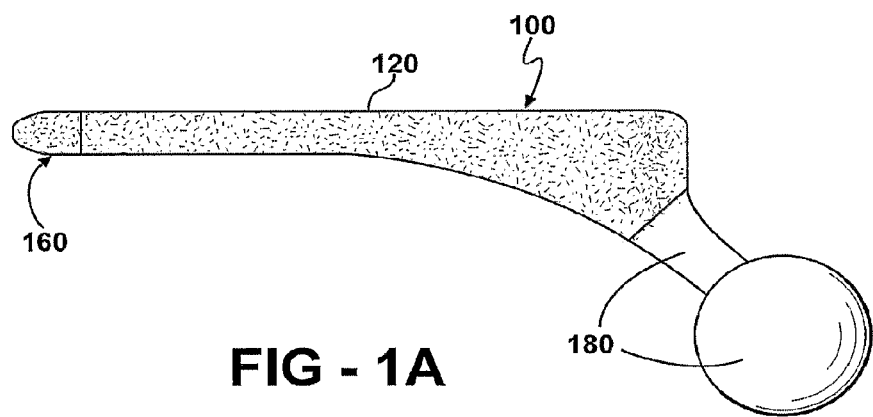
FIG. 1A is a line drawing of an apparatus according to an embodiment of the invention in the form of a hip joint implant showing an exterior view of the implant.

FIG. 1A shows an external view of a hip implant body 100 illustrating a metal coating, such as a silver coating, shown as stippling, present on an external surface 120 of the implant body. The coating is present on the cap 160 as well in this illustration but not on articular or wear surfaces as shown at 180.

A conduit from one terminal of the power source to a metal component is optionally provided in the form of a wire extending there-between. As noted above, a further connection between the metal component and a second terminal of the power source is optionally provided.

In a further preferred embodiment of the invention, a metal component is in removable contact with the implant. For example, a metal component in removable contact with an implant may have the form of a metal wire in contact with an implant surface.

In another embodiment of an inventive system, a conduit is provided which extends outside of the body of an individual having an implant prosthesis according to the invention. For example, a conduit is provided in the form of a wire such that one end of the wire may be positioned in proximity to the metal component of an implanted prosthesis, preferably in contact with the metal component in order to deliver current and release metal ions from the metal component. The opposite end of the wire optionally may extend outside the body to contact a power source. The conduit is optionally removed when risk of infection is low and may be repositioned for stimulation of metal ion release as desired.

Figure 2:
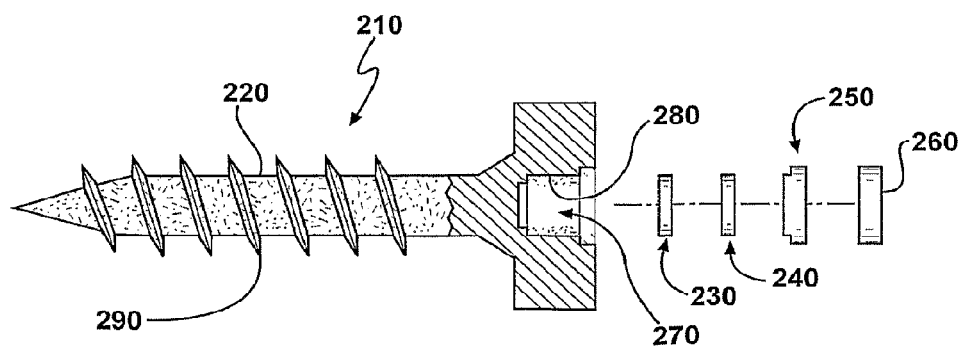
FIG. 2 is a line drawing of an inventive bone screw implant system.

FIG. 2 illustrates an implant body in the form of a fixation device, particularly, a bone screw 210. An external surface 220 of the implant body includes a metal component in the form of a continuous metal coating, including coating on screw threads. Also shown is a switch 230, a resistor 240 and a battery 250 inserted in an internal cavity 270 shown in the cut away region marked by stripes. Also shown is a cap 260 for closing the cavity and protecting the components disposed in the cavity from the external environment, as well as limiting exposure of cells to the components disposed in the cavity. A metal coating 280 is shown inside the cavity 270. An embodiment in which a metal coating is also present on the threads 290 of the illustrated bone screw is depicted in this illustration.

The configurations shown in FIGS. 1 and 2 allow for a dead end electrical circuit between the battery and the external silver surface. Current will flow through the better conductor, the silver coating, to the external surface and thus avoid the much poorer conductor, the internal residual hardware device. However, it has been found that embodiments which do not include a dead end circuit produce improved antimicrobial effects.

In a highly preferred embodiment, an inventive medical implant system includes an insulator such that current flowing from a first terminal is prevented from creating a short circuit. Thus, an insulator is placed in a current path from the first terminal of a power source in order to prevent current from reaching the second terminal without completing a circuit including a conductive body tissue or fluid in the vicinity of the implanted implant system.

Figure 3:
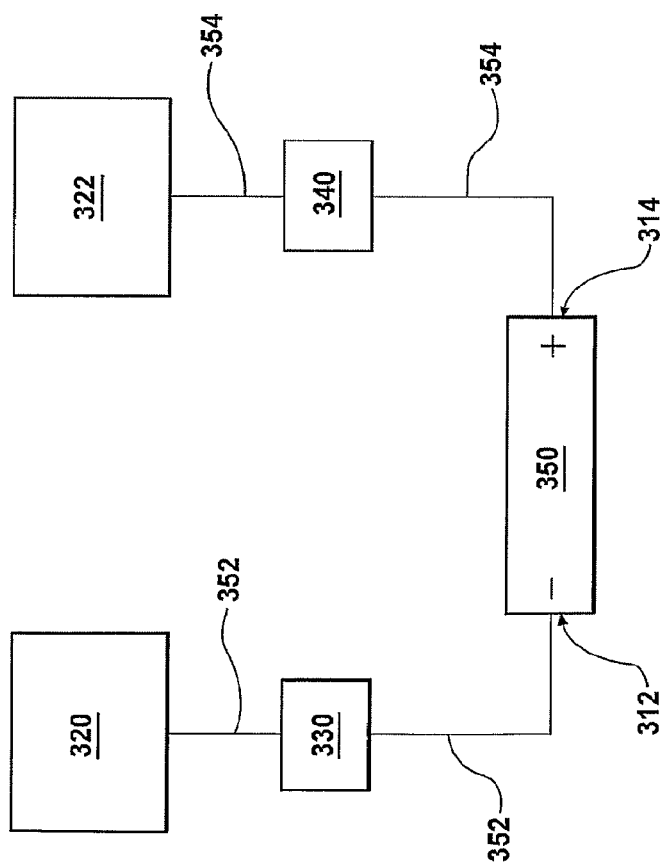
FIG. 3 is a schematic circuit diagram of a preferred version of an implant system according to the present invention.

FIG. 3 illustrates a schematic circuit diagram of such a highly preferred embodiment. A first metal component disposed in electrical connection with a first element of an implant body is shown at 320 and a second metal component disposed in electrical connection with a second element of an implant body is shown at 322. Each of the metal components 320 and 322 is in electrical communication with a power source 350, the first metal component 320 in electrical communication with a first terminal 312 of the power source 350 and the second metal component 322 in electrical communication with a second terminal 314 of the power source 350. Conduits 352 and 354 illustrate electrical connectors between the first and second metal components 320 and 322 and the first and second terminals 312 and 314, respectively, of the power source. Also illustrated are an optional resistor 330 and an optional switch 340, each in electrical communication with the power source.

Joint replacement or repair implants include one or more implantable parts which may be included as an implant body in an inventive system. For example, a hip joint replacement implant typically includes a femoral part, replacing the natural femoral head, and a socket part, or acetabular cup or shell, replacing the natural acetabulum. While an inventive system is extensively discussed herein with regard to an implant body which is a femoral part of a hip joint replacement prosthetic implant, it is appreciated that the socket part, or cup portion of a hip implant prosthesis may also be included in an inventive system and configured to include an internal cavity containing a power source and other components as described herein. A further example of joint replacement implant parts include a wrist implant having a carpal component, for instance present where a first row of carpal bones is removed, and a radial part, for instance inserted or attached to the radius bone. The radial part may provide an articular surface for interaction with a carpal part. Another example is a knee joint prosthetic implant, having a femoral part attached to the femur and a tibial part attached to the tibia, each having an articular surface for interaction with the other. It is appreciated that one or more parts of an implant prosthesis may be configured to include an internal cavity containing a power source and other components as described herein. Thus, an inventive system may include more than one implant body. In a further option, each of the multiple implant bodies may include a cavity and power source, and may further include other components, preferably a resistor and switch, as described. In a further option, multiple switches may be controlled separately, for instance where one implant body or region in the vicinity of the implant body is more vulnerable to infection than another, a switch in that implant body may be activated to turn on current in that implant body without turning on current in another implant body.

As noted, an implant may be a temporary implant, intended to remain implanted for a limited period of time, or a permanent implant, intended to remain implanted long-term, even as long as the remainder of the individual's life. One type of temporary implant is known as a "spacer" implant. A spacer implant typically has a similar size and shape compared to a permanent or short-term implant. A spacer implant is typically implanted in order to maintain the spatial integrity of an area where a permanent joint replacement implant will be positioned eventually. For example, where an individual has a badly infected implant which must be removed, a spacer implant may be implanted while the infection is being fought.

An inventive system is particularly advantageous in such a situation since a synergistic effect of an inventive antimicrobial system with a course of systemic or local antibiotics is achieved. Further, an inventive spacer implant may lessen or eliminate the need for use of bone cement, currently used in this situation. The insertion of a spacer implant would allow the patient to be much more active than if the joint were filled with bone cement. Further, tissue encroachment at the site is decreased by placement of a spacer implant.

In one embodiment, a power source, such as a battery, having a first terminal, a second terminal, and a potential difference between the first and second terminals, is provided. Further provided is a conduit for an electrical connection between the first terminal and the metal component. Also provided is a conduit for an electrical connection between the metal component and the second terminal.

In a preferred embodiment, an electrical circuit is completed between the metal component and the second terminal through a tissue or fluid of a body in which an inventive system is implanted.

As noted above, in a highly preferred embodiment, an inventive medical implant system includes an insulator such that current flowing from a first terminal is prevented from creating a short circuit. Thus, an insulator is placed in a current path from the first terminal of a power source in order to prevent current from reaching the second terminal without completing a circuit including a conductive body tissue or fluid in the vicinity of the implanted implant system.

In a particular example, referring to FIG. 4, an implant body is shown in the form of a fixation device, particularly, a bone screw 400. An external surface 420 of the implant body includes a metal component in the form of a continuous metal coating, including coating on screw threads. Also shown is a switch 430, a resistor 440 and a battery 450 inserted in an internal cavity 470. The battery has a first terminal 412 and a second terminal 414. Also shown is a cap 460 for closing the cavity and protecting the components disposed in the cavity from the external environment, such as body tissue or fluids 422, as well as limiting exposure of cells to the components disposed in the cavity. Further shown is an insulator 485. In this example, a current path is established from the first terminal 412 of the battery 450 through the implant body 410 which serves as a conduit for current to a metal component 420, and continuing through the body tissue or fluids 422 in which the implant is located and through the cap 460 to the second terminal 414 of the battery 450. The insulator 485 prevents short circuiting of the current, for instance through the implant body to the second terminal of the battery 414. FIG. 4A shows insulator 485 viewed along broken line 498 shown in FIG. 4. The insulator 485 shown in FIG. 4A includes a conductive portion 487 configured such that current can pass through to the second terminal 414. Such a conductive portion may be a portion made of a conductive material. In another option, a conductive portion may be an opening through a non-conductive region of the insulator.

In another particular example, FIG. 5 illustrates an implant body in the form of a hip implant 500. An external surface 520 of the implant body includes a metal component 520 in the form of a continuous metal coating. Also shown is a switch 530, a resistor 540 and a battery 550 inserted in an internal cavity 570. The battery has a first terminal 512 and a second terminal 514. Also shown is a cap 560 for closing the cavity and protecting the components disposed in the cavity from the external environment, such as body tissue or fluids 522, as well as limiting exposure of cells to the components disposed in the cavity. Further shown is an insulator 585. In this example, a current path is established from the first terminal 512 of the battery 550 through the implant body 510 which serves as a conduit for current to a metal component 520, and continuing through the body tissue or fluids 522 in which the implant is located and through the cap 560 to the second terminal 514 of the battery 550. The insulator 585 prevents short circuiting of the current, for instance through the implant body to the second terminal of the battery 514. FIG. 5A shows insulator 585 viewed along broken line 598 shown in FIG. 5. The insulator 585 shown in FIG. 6A includes a conductive portion 587 configured such that current can pass through to the second terminal 514. Such a conductive portion may be a portion made of a conductive material. In another option, a conductive portion may be an opening through a non-conductive region of the insulator.

Optionally, an insulator is configured to provide a threaded fit into an internal cavity, thus insulating a cap from the walls of the cavity and thereby insulating the cap from the implant body. For example, an insulator in the form of a threaded insert such as a Helicoil, is provided for threaded engagement with a wall of an internal cavity and non-threaded engagement with the wall of a cap.

An insulator may be made of any non-electrically conductive material. Optionally, an insulator is made of a biocompatible material. Suitable materials include ceramics, plastics and other polymers, such as rubber. An insulator may be provided in any of various forms in order to prevent short circuiting in an inventive implant system. For example, an insulator may be a body of a non-electrically conductive material disposed in the current path between the first terminal of the power source and the second terminal of the power source preventing current flowing from the first terminal from reaching the second terminal without completing a circuit including a conductive body tissue or fluid adjacent to the external surface of the implant system when implanted in a patient body. Further, an insulator may be a coating of a non-conductive material disposed in the current path.

FIG. 6 illustrates an apparatus 600 according to an embodiment of the invention in the form of a hip joint implant showing an exterior view of the implant. A hip implant is shown having a metal-containing coating 620, depicted as stippling, on the external surface. Three sections of the hip implant are shown, a main body 630, an intermediate insulator section 640 and a cap 660. The insulator section 640 electrically insulates the first metal component, the antimicrobial metal-containing coating on the main body 630 from the second metal component, the antimicrobial metal-containing coating on the cap portion 660. In the illustrated embodiment, the surface 622 and body of the intermediate section 640 is an insulator in the current path between the first and second terminals of a power source. An internal cavity 670 is indicated. This cavity allows for the internal placement of the battery, switch and resistor components. In this embodiment, main body 630 and the cap 660 each include a male connector 680 for secure attachment of the main body 630 to the intermediate insulator section 640 and for secure attachment of the cap 660 to the intermediate insulator section 640. As depicted, the male connectors 680 are threaded for reciprocal engagement with a threaded portion of the intermediate insulator section 640. Any type of connector may be used however, illustratively including "snap" fitting of the components. Assembly of the main body 630, intermediate insulator section 640 and cap 660 forms a hermetic seal for the cavity such that components internal to the cavity are protected from the external environment and the patient's body is protected from exposure to the components in the cavity. No metal component is present on surfaces tending to wear due to interaction with other implant parts or natural elements of the body as shown by sections without stippling at 690.

FIG. 7 illustrates an interior view of a portion of an implant such as shown in FIG. 6. The three sections of the hip implant described in FIG. 6, a main body 630, an intermediate insulator section 640 and a cap 660 are shown in section, along with male connectors 680 in reciprocal engagement with a threaded portion of the intermediate insulator segment 640. An internal cavity 670 is also shown. Shown in the internal cavity 670 are a switch 612, a resistor 614, and a power source in the form of a battery 618. In the illustrated embodiment, a metal component 620 in the form of a metal-containing coating is present on the surface of the main body 630 and a metal component 621 in the form of a metal-containing coating is present on the surface of the cap 660. The metal component 620 is in electrical communication with power source terminal 623 and the metal component 621 is in electrical communication with power source terminal 624. The intermediate insulating section 640 insulates the main body portion 630 from the cap 660, preventing current flowing from the first terminal from reaching the second terminal without completing a circuit including a conductive body tissue or fluid adjacent to the external surface of the implant system when implanted.

Figure 8:
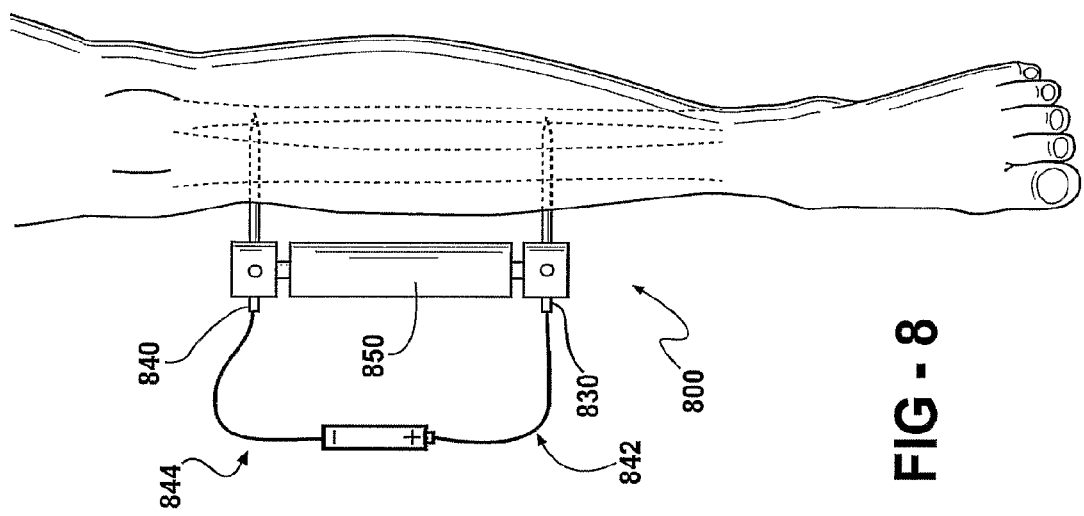
FIG. 8 is a line drawing of an external fixation device illustrated in situ.

FIG. 8 illustrates an implant system according to the present invention in the form of an external fixation device 800. Depicted is a first element in the form of a fixation rod 830, electrically connected to a first terminal of power source 818 by a conduit 842. A second element 840 is electrically connected to a second terminal of the power source 818 by a conduit 844. A structural support 850 for fixation rods 830 and 840 is illustrated. Fixation rods 830 and 840 are electrically isolated from each other. In particular, support 850 includes a non-conductive material such that current does not pass from a fixation rod through the support 850 to a second fixation rod.

Figure 9:
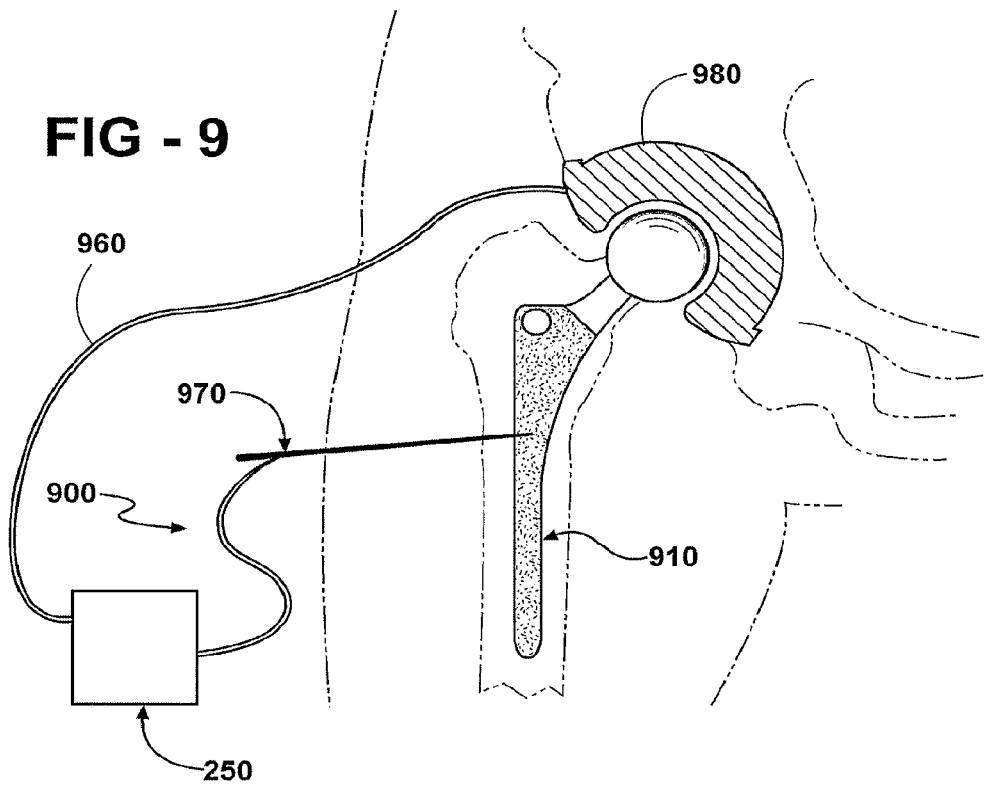
FIG. 9 is a line drawing of an apparatus according to an embodiment of the invention in the form of a hip joint implant having a power source external to the body of the patient.

FIG. 9 illustrates an inventive system 900 in the context of a human body including an external power supply 950 and a conduit 970 contacting an implant body 910 having a metal coating, shown as stippling, on a portion of the surface of the implant body 910. It will be noted that no coating is present on an acetabular wear surface of the implant prosthesis. Further shown is the "cup" portion 980 of a hip replacement implant, marked by stripes. A lead 960 is shown electrically connecting these two portions of a hip implant. Alternatively, an insulator may be disposed at another location in the current path, such as between two portions of the implant body 910, for instance as shown in FIG. 5. In a further alternative embodiment, power supply 950 may be implanted.

Figure 10:
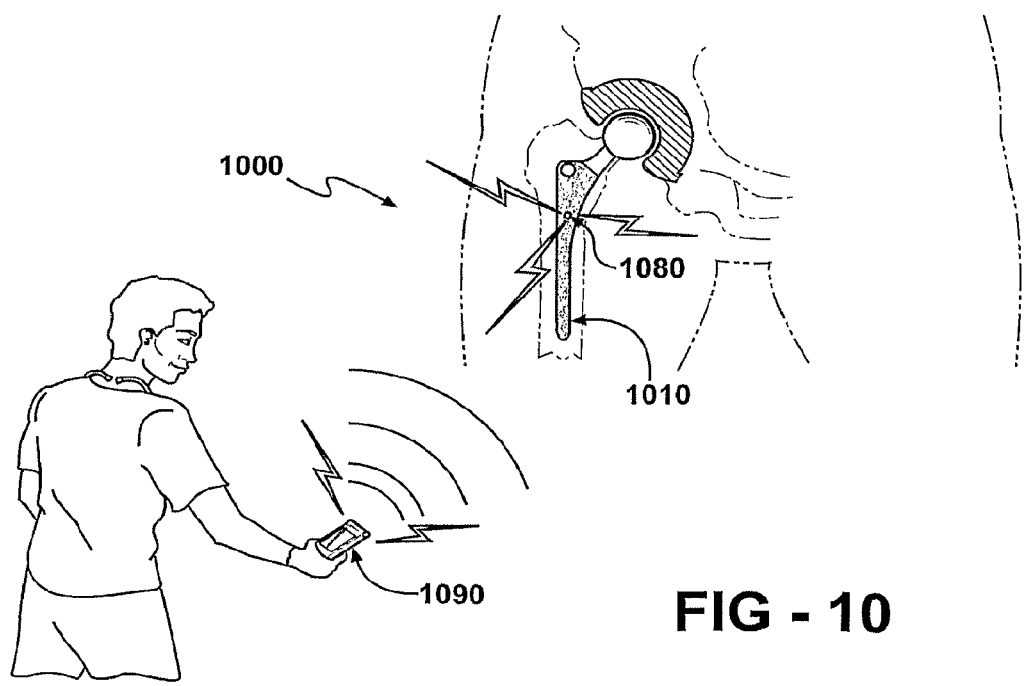
FIG. 10 is a line drawing of a hip joint implant apparatus according to an embodiment of the invention, showing transmission of a signal to the apparatus in situ.
Figure 11:
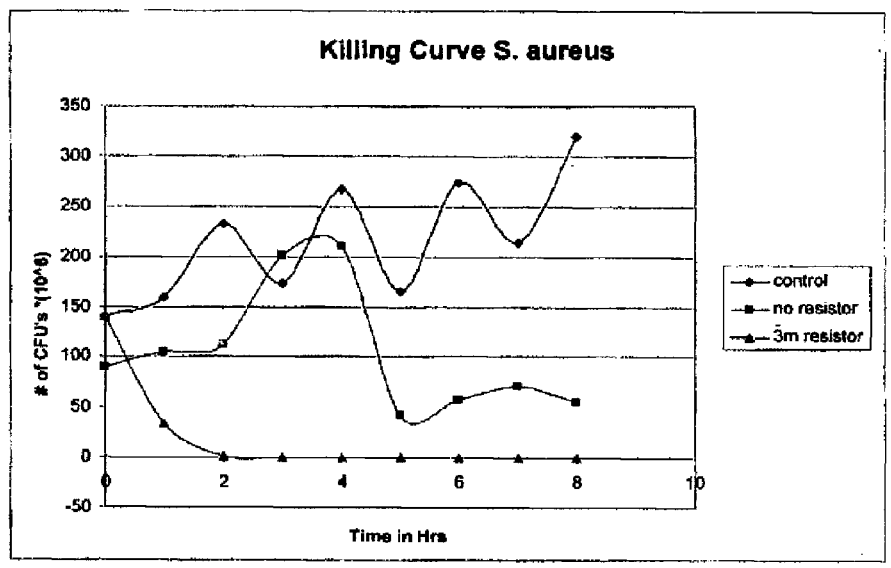
FIG. 11 is a graph illustrating a "killing curve" of *S. aureus*.
Figure 12:
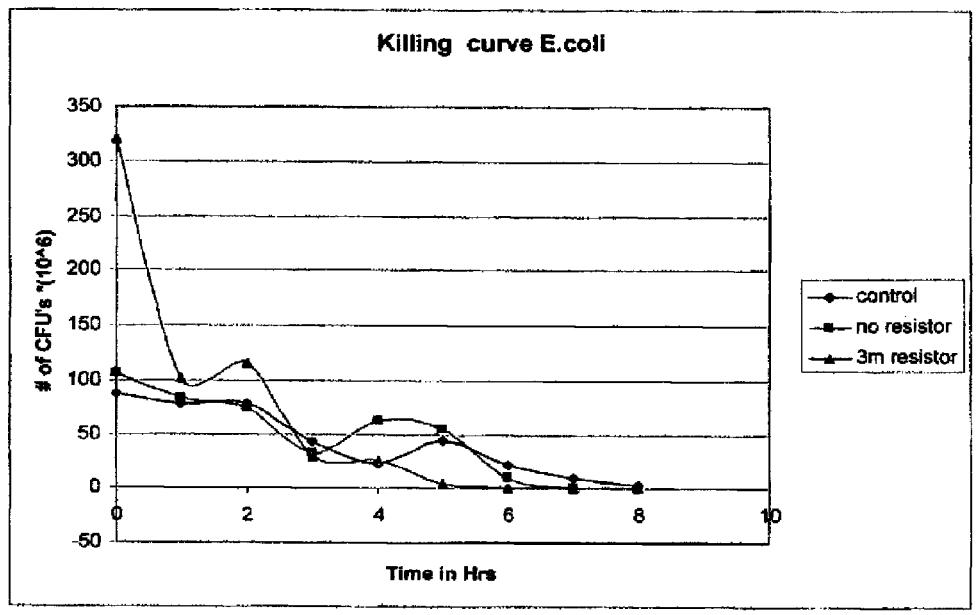
FIG. 12 is a graph illustrating a "killing curve" of *E. coli*.

Another embodiment of an inventive apparatus is shown in FIG. 10 which shows an inventive system 1000 including a hip replacement prosthesis 1010 in the context of a human body. Also shown is an external controlling device 1090 which may be used to modulate current flow in an implanted prosthesis by acting on internal circuitry 1080 in order to modulate delivery of metal ions to inhibit microbes. In a preferred embodiment of such a system, an insulator is positioned in the current path between two components of the implant.

A method for inhibiting microbial infection associated with an orthopedic implant is provided which includes providing an inventive system as described and delivering a current to a metal component disposed on an external surface of an implant body, the implant body located in a human body at a site of potential infection.

In one embodiment, an inventive method for inhibiting an infectious organism includes introducing an electrical current into a metal component of an implanted joint prosthesis to release metal ions from the component. The metal ions have a biostatic or biocidal effect on microorganisms such that growth and/or attachment of microorganisms on the implant and in the vicinity of the implant are inhibited. A method according to the present invention is a method of treating osteomyelitis associated with an implant in one preferred embodiment.

As noted above, biocidal metals and ions include transition metals and ions. Preferred metals and ions include silver, copper, cadmium and combinations thereof. Further, metals and ions such as cobalt, nickel, platinum, gold, zinc, palladium, manganese, chromium, and other transition metals and/or Periodic Table column 10-14 metals may be included.

In one embodiment, a method of inhibiting a microbial infection is provided which includes providing an inventive implant system and delivering a current to a silver-containing metal component disposed on an external surface of an implant body, the implant body located in a human body at a site of potential infection. In particular, such a method is applicable to inhibit infections by Gram negative bacteria, Gram positive bacteria, and fungus which are associated with implants. Such microbes illustratively include such bacteria illustratively include *Esherichia coil, S. aureus, Pseudomonas aeruginosa, Enterococcus faecalis*, Methicillin resistant *S. aureus* (MRSA) and *Candida albicans*.

In a further embodiment, a method of inhibiting a microbial infection is provided which includes providing an inventive implant system and delivering a current to a copper-containing metal component disposed on an external surface of an implant body, the implant body located in a human body at a site of potential infection. In particular, such a method is applicable to inhibit infections by Gram positive bacteria which are associated with implants. Such bacteria illustratively include *S. aureus, Enterococcus faecalis*, and Methicillin resistant *S. aureus* (MRSA).

In another embodiment, a method of inhibiting a microbial infection is provided which includes providing an inventive implant system and delivering a current to a copper and cadmium and/or silver and cadmium containing metal component disposed on an external surface of an implant body, the implant body located in a human body at a site of potential infection.

Infectious organisms inhibited by such metals and metal ions illustratively include bacteria, mycobacteria, viruses and fungi. Methods and apparatus according to the present invention are particularly useful in cases involving antibiotic resistant organisms.

Generally, such metal ions inhibit infection at concentrations ranging between $1\times10^{-3}$ M-$1\times10^{-7}$ M, inclusive, and is preferably delivered in amounts sufficient to achieve a concentration in this range. Optionally, and preferably, metal ions are delivered in amounts sufficient to achieve a concentration in the range between $5\times10^{-5}$ M-$0.25\times10^{-6}$ M, inclusive. In particular, silver ions are delivered in amounts sufficient to achieve a concentration in the range between $5\times10^{-5}$ M-$0.25\times10^{-6}$ M, inclusive.

A metal ion is released from a metal component by application of an electrical current to the metal component. Bone and soft tissue cells are affected by electrical current and thus the amount of current delivered and the length of time for which it is delivered must be considered in the context of the proximity of the implant to such cells. The amount of a metal ion released is dependant on the strength and duration of the electrical stimulus which is adjusted accordingly.

Generally, a current in the range of 0.1 microamps to 200 milliamps is delivered to a metal component. In general, a current is delivered to a metal component for periods of time ranging from about 1 minute to continuous delivery over the lifetime of the power source, that is, weeks, months or years. In general weaker currents are used for longer-term treatments. Thus, in a preferred embodiment, 0.3-1.5 microamperes of current is delivered in order to ionize a silver surface layer. Also preferred is an embodiment in which 0.8-1.2 microamps of current is delivered to a silver coating.

Small electrical currents in the ranges described are sufficient to ionize a solid silver coating, producing silver ions. Without wishing to be bound by theoretical considerations, according to Faraday's law, under ideal conditions 4 micrograms of silver will be liberated per hour per micro ampere of current applied to silver. Calculation 1 below details this.

$$(1\ \mu AMP) * \left(\frac{1\ Coulomb}{1\ Amps * Sec}\right) * \left(\frac{1\ Faraday}{96,487\ Coulombs}\right) * \left(\frac{107.868\ gramAG}{1\ Fraday}\right) * \left(\frac{1 * 10^6\ \mu g}{1\ g}\right) * \left(\frac{36000\ Sec}{Hour}\right) = 4.02\ \mu g/hour \quad \text{(Equation 1.0)}$$

Assuming the power source is capable of producing a 1 micro-ampere current and that the electrical current should not exceed 20 micro-amperes at any time, 10 micrograms/milliliter concentration of silver ions within a couple of hours. Additionally the maintenance of a 10 micrograms/milliliter concentration of silver ions is possible with very small electrical current requirements.

Additional theoretical considerations indicate that total lifetime exposure to silver ions advantageously do not exceed 8.95 grams for a person of average size, approximately 70 kilograms, and having an average life expectancy, about 70 years. This calculation is based on the assumption that about 0.35 milligrams of silver can be safely consumed each day, see Newman, J. R., Tuck Silver 100 Safety Report, Jan. 9, 1999. Thus, for a permanent implant, it is desirable that an inventive system not contain more than about this amount of silver. Similar calculations may be made for other metal ions as will be recognized by one of skill in the art. For example, such a calculation indicates that 2.37 micrograms per hour of copper per micro ampere of current applied.

In one embodiment, a method of inhibiting bacterial infection associated with an implant includes administration of a systemic or local antibiotic and administration of a metal antibiotic via an inventive implant. A synergistic effect of such treatment is achieved as a lower dosage of both the systemic or local antibiotic and the metal antibiotic is necessary to achieve a therapeutic effect.

While inventive methods, implants and implant systems are generally described with reference to use in humans herein, the methods and apparatus are also used in other animals to inhibit infection. For example, an inventive apparatus and method is used in animals illustratively including cats, dogs, cattle, horses, sheep, goats, rats, and mice.

The apparatus and methods described herein are presently representative of preferred embodiments, exemplary, and not intended as limitations on the scope of the invention. Changes therein and other uses will occur to those skilled in the art. Such changes and other uses are encompassed within the spirit of the invention as defined by the scope of the claims.

EXAMPLE 1

One embodiment of an implant body is manufactured by obtaining a hip replacement prosthesis similar to a DePuy AML Hip System designed to include an internal cavity, about 10 millimeters in length and about 5 millimeters in width and a cap to close the opening of the cavity as described herein. Articular surfaces of the implant body are masked and the remaining external surfaces are coated with a silver metal film about 1 micron in thickness. A battery, resistor and switch are chosen to fit in the cavity. A portion of the cavity wall adjacent to the external surface of the implant body is also coated with silver metal to a depth adjacent the positive terminal of the battery. An insulator is positioned such that short-circuiting is avoided.

A battery with the desired profile is currently in production by many battery manufacturers. The Energizer battery number 337 satisfies all of the required size characteristics needed for implementation within a bactericidal hip implant. When examining the Energizer 337 battery one can see that the small size, 1.65 mm in height by 4.8 mm in diameter allow the battery to easily fit within the 5 mm compartment.

The 337 size battery provides a voltage of 1.55 volts, which is much greater than required for the application of ionizing a solid silver coating. Thus, a resistor is chosen to be placed in series with the battery. Using a voltage of 1.55 volts and a required current of 1 micro-ampere one can calculate the required resistor as shown in Equations 2.1 and 2.2 below.

$$V = IR \quad \text{(Equation 2.0)}$$

$$R = \frac{V}{I} = \frac{1.55\ \text{volt}}{1 * 10^{-6}\ \text{amperes}} = 15,550,000\ \text{ohms} \quad \text{(Equation 2.1)}$$

The required resistor should have a resistance of approximately 15.5 mega-ohms. Additionally the resistor must conform to the size requirements as set by the diameter of the pocket within the shaft of the implant, 5 millimeters.

Utilizing a resistor with the required 15.5 mega-ohms rating in series with the 337 battery will provide for approximately 75573 hours of run time. The calculation of the run time for the battery under with this resistance is show in calculation #3 below. During this running time the battery will be producing the required 1 micro-ampere current that is required to ionize the solid silver coating.

$$\frac{\text{run\_Time(New\_hip)}}{MMCO8 - \text{Resitance}} = \frac{\text{run\_Time(simulated\_application}}{\text{simulated} - \text{resistance}} \quad \text{Equation (3.0)}$$

$$\frac{\text{run\_Time(New\_hip)}}{15,550,000\Omega} = \frac{486\_\text{hours}}{100,000\Omega} \quad \text{Equation (3.1)}$$

$$\text{run\_Time(New\_hip)} = 75573\_\text{hours} \quad \text{Equation (3.2)}$$

An included switch, like all other components, fits within the 5 millimeter diameter cavity that has been machined within the shaft of the original hip implant. Additionally the switch will have the ability to be turned ON and OFF once implanted within the human body. In this example, a magnetically based switch is selected. Coto Technology manufactures a switch, RI-80 Series Dry Reed Switch that is designed specifically for medical applications and which meets the design size constraints. The switch has a maximum dimension of the central tube of 5 millimeters in length and 1.8 millimeters in diameter. This switch will carry a maximum current of 0.5 amperes and a has a maximum operating voltage of 200 volts, both of which are satisfactory operating characteristics needed for a bactericidal hip implant according to the invention.

EXAMPLE 2

Procedures to identify an antimicrobial metal composition may include an examination of each metal's antimicrobial potential using a panel of common Gram (+) and Gram (−) bacterial, fungal species or other microbes. a method adapted from the Kirby Bauer agar gel diffusion technique, the antimicrobial efficacy of eight metals: silver, copper, titanium, gold, cadmium, nickel, zinc and stainless steel AISI 316L and their electrically generated ionic forms are tested against 5 bacterial species and one fungus commonly associated with osteomyelitis.

Strains of *Esherichia coli, S. aureus, Pseudomonas aeruginosa, Enterococcus faecalis*, Methicillin resistant *S. aureus* (MRSA), and *Candida albicans* isolated from samples submitted to the Pennsylvania State University Animal Diagnostic Laboratory (*E. coli, S. aureus, P. aeruginosa* and *E. faecalis*) or J.C. Blair Hospital, Huntingdon, Pa. (MRSA and *C. albicans*), are diluted to a 0.5 MacFarland standard and inoculated onto Mueller-Hinton agar plates (Remel, Lenexa, Kans.).

Metallic wires served as the ion source, specifically: silver (99.97% purity), copper (99.95+% purity), titanium (99.8% purity), gold (99.99% purity), cadmium (99.999% purity), nickel (99.98% purity), zinc (99.999% purity) and stainless steel AISI 316L. All wires are of uniform equal diameter (1.0 mm).

Small holes are burned into opposite sides of the Petri plates which allowed for the aseptic threading of 32 mm lengths of test wire into the agar. Once embedded, 1 cm² of wire surface area is exposed to the growing microbes.

Electrical currents are generated by placing a standard 1.55 Volt AA battery in series with one of the following resistors: 3.01 MΩ, 1.5 MΩ, 150 kΩ, and 75 kΩ. A 70 mm length of each of the test metals is connected in series with the given resistor. The current that is generated by each of the four different resistors (3.01 MΩ, 1.5 MΩ, 150 kΩ, and 75 kΩ) is 0.5 µA, 1.0 µA, 10 µA, and 20 µA respectively. The 20 µA/cm² surface area charge is proven in 1974 to be a safe electrical exposure value for the cells. (Barrnco 1974) As calculated with Faraday's equation, a 20 µA/cm² surface area charge density produced over 80 µg/hour of silver ions.

The circuit is completed by aseptically threading the anode through the opposite hole and embedding it into the agar. One control plate for each microbial species is aseptically threaded with wires, but received no electrical current. The plates are incubated in ambient air at 37° C. for 24 hours, and subsequently examined for bacterial growth and/or zones of inhibition.

Of the eight metals and metal ions tested, silver ions and cadmium show bactericidal efficacy against all bacterial species tested, and copper ions showed bactericidal efficacy against Gram-positive bacteria. Titanium, gold, nickel, zinc and stainless steel AISI had no significant effects in this example.

Exemplary results are shown in Table 1 in which numbers represent measurements of the diameter of the zone of inhibition in millimeters around the central wire. The table shows that silver has some microbicidal properties when not electrically ionized, since *E. coli* is inhibited by non-charged silver. A smaller current produced results similar to larger currents, and in all cases the addition of current increased the size of the inhibition zone.

Copper also shows antimicrobial properties, both in the ionic form and the uncharged metallic form, as summarized in Table 1. In the uncharged form copper showed bactericidal properties against *E. faecalis*. A minimal current produced bactericidal results for all Gram (+) species of bacteria, and higher currents produced larger zones. Copper did not have an effect on Gram (−) bacterial species at currents used.

Surprisingly, cadmium results are unique in producing antimicrobial effects against all organisms tested, and the pattern of efficiency held true both in the absence and presence of electrical stimulation. Increasing the current resulted in minimal changes in microbial response. Cadmium produced a double zone of inhibition: an inner zone of complete clearing closer to the wire, and an outer zone of decreased bacterial growth (incomplete clearing). For descriptive purposes, the inner zone is considered to be "microbicidal", while the outer zone is considered "microbistatic", or inhibitory. Numbers shown in Table 1 reflect this double zone of inhibition such that the size of the "inner zone" is present first and the size of the "outer zone" is presented in parentheses. Additionally, cadmium consistently showed some inhibitory effect in the absence of electrical charge; increasing the current had little additional effect.

TABLE 1

| | Gram Positive | | | Gram Negative | | Fungus |
|---|---|---|---|---|---|---|
| Current | S. aureus | E. faecalis | MRSA | E. coli | P. aeruginosa | C. albicans |
| Silver | | | | | | |
| 0 uA | 6 | 0 | 0 | 5 | 0 | 0 |
| 0.5 uA | 18 | 17 | 18 | 20 | 18 | 34 |
| 1 uA | 20 | 19 | 18 | 21 | 21 | 30 |
| 10 uA | 20 | 21 | 18 | 25 | 21 | 32 |
| 20 uA | 20 | 20 | 18 | 24 | 20 | 30 |
| Gold | | | | | | |
| 0 uA | 3 | 0 | 0 | 0 | 0 | 0 |
| 0.5 uA | 0 | 0 | 0 | 0 | 0 | 0 |
| 1 uA | 0 | 0 | 0 | 10 | 0 | 0 |
| 10 uA | 0 | 0 | 0 | 0 | 0 | 0 |
| 20 uA | 0 | 0 | 0 | 0 | 0 | 0 |
| Titanium | | | | | | |
| 0 uA | 0 | 0 | 0 | 0 | 0 | 0 |
| 0.5 uA | 0 | 0 | 0 | 0 | 0 | 0 |
| 1 uA | 0 | 0 | 0 | 0 | 0 | 0 |
| 10 uA | 0 | 0 | 0 | 0 | 0 | 0 |
| 20 uA | 0 | 0 | 0 | 0 | 0 | 0 |
| Copper | | | | | | |
| 0 uA | 0 | 11 | 0 | 0 | 0 | 0 |
| 0.5 uA | 14 | 16 | 7 | 0 | 0 | 0 |
| 1 uA | 6 | 16 | 6 | 0 | 0 | 0 |
| 10 uA | 0 | 15 | 9 | 0 | 0 | 0 |
| 20 uA | 8 | 18 | 11 | 0 | 0 | 0 |
| Stainless steel | | | | | | |
| 0 uA | 0 | 0 | 0 | 0 | 0 | 0 |
| 0.5 uA | 0 | 0 | 0 | 0 | 0 | 0 |
| 1 uA | 0 | 0 | 0 | 0 | 0 | 0 |
| 10 uA | 0 | 0 | 0 | 0 | 0 | 0 |
| 20 uA | 0 | 0 | 0 | 0 | 0 | 0 |
| Cadmium | | | | | | |
| 0 uA | 8(15) | 5 | 14 | 6(18) | (17) | 28 |
| 0.5 uA | 6(10) | 6 | 13 | 5(18) | (12) | 28 |
| 1 uA | 8(15) | 6 | 13 | 4(18) | (18) | 31 |
| 10 uA | 6(14) | 5 | 15 | 6(18) | (16) | 30 |
| 20 uA | 7(15) | 5 | 16 | 5(17) | (18) | 30 |

TABLE 1-continued

|  | Gram Positive | | | Gram Negative | | Fungus |
| --- | --- | --- | --- | --- | --- | --- |
| Current | S. aureus | E. faecalis | MRSA | E. coli | P. aeruginosa | C. albicans |
| Zinc | | | | | | |
| 0 uA | 0 | 0 | 0 | 0 | 0 | 0 |
| 0.5 uA | 0 | 0 | 0 | 0 | 0 | 0 |
| 1 uA | 0 | 0 | 0 | 0 | 0 | 0 |
| 10 uA | 0 | 0 | 0 | 0 | 0 | 0 |
| 20 uA | 0 | 0 | 0 | 0 | 0 | 0 |
| Nickel | | | | | | |
| 0 uA | 0 | 0 | 0 | 0 | 0 | 0 |
| 0.5 uA | 0 | 0 | 0 | 0 | 0 | 0 |
| 1 uA | 0 | 0 | 0 | 0 | 0 | 0 |
| 10 uA | 0 | 0 | 0 | 0 | 0 | 0 |
| 20 uA | 0 | 0 | 0 | 0 | 0 | 0 |

EXAMPLE 3

Characterization of Effective Antimicrobial Metals

A "killing curve analysis" may be performed in order to characterize parameters which achieve an antimicrobial effect. A predetermined number of colony forming units/ml (CFU/ml), established in a growth medium, are transferred to a saline solution and then exposed to the antimicrobial metal or metal form. At predetermined time intervals, an aliquot is removed, diluted (if necessary), inoculated onto blood agar plates and incubated overnight at 37° C. The resulting growth is quantified as CFU/ml. A graph, with time as the X-axis and CFU/ml as the Y-axis demonstrates the point at which the antimicrobial effect and microbial population growth intersect. The concentration of metal required for antimicrobial effect can be determined by examining the time point at which the microbial population begins to decrease.

To examine the rate of diffusion of ions away from the metal source, i.e. the rate at which the microbes are inhibited from growing (or killed), high performance microscopy may be used. A high performance microscopic system developed by Cytoviva allows for real-time observation of living cells and cellular components without the use of staining agents. By observing the microbial response to a given metal, a "velocity" of microbial destruction can be directly observed. The rate of diffusion of ions through agar can be inferred from the velocity of kill.

In this example, silver is tested with respect to two different bacterial species, E. coli and S. aureus. A current of 0.5 uA is used in this example.

Strains of E. coli and S. aureus isolated from samples submitted to the Pennsylvania State University Animal Diagnostic Laboratory, are separately diluted to a 0.5 Mac-Farland standard and added to individual test tubes containing 10 mls of sterile Tryptic Soy Broth (TSB). A silver wire (99.97% purity) having a uniform diameter of 1.0 mm served as a source of ions.

Two small holes are burned into the screw cap of each test tube. Silver Wires (99.97% purity), having uniform diameters of 1.0 mm, served as ion sources. The wires are aseptically threaded through the screw cap holes and positioned to expose a total length of 32 mm into the previously inoculated TSB. This resulted in the exposure lo 1 cm$^2$ of silver wire to growing bacterial cells. Electrical current is generated by placing a standard 1.55 Volt AA battery in series with a 3.01 MO resistor. The current that is generated by the 3.01 MΩ resistor is 0.5 µA when combined into the circuit. Additionally a circuit, formed without any resistor is utilized and inserted into a tube in an identical fashion. The circuits are completed by aseptically threading the anode through another hole in the test tube screw cap and into the TSB. One tube of each bacterial species, served as the control. It contained a silver wire, but no external circuit is connected. The silver wire as well as the anode wire is placed in contact with the bacterially laden broth continued within the test tube. This setup is used to produce "killing curves".

The tubes are incubated in air at room temperature for a total of 8 hours. Every hour the test tube is vortexed for approximately 10 seconds. The test tube cap is then opened and a 10 µl sample of broth is aseptically drawn from the test tube. The test tube are again closed and vortexed. The sample is plated onto blood agar plates using a spiral plating technique. The blood agar plates are incubated at room temperature for 24 hours. The number of colonies present on the blood agar plates at 24 hours are counted and recorded.

The results clearly demonstrate that the charged form of the silver metal has a much greater kill rate when compared to the non-charged material. A "killing curve" shown in FIG. 9 shows the killing rate associated with S. aureus. The results clearly demonstrate a bacterial reduction rate of approximately 5.698*10E12 bacteria per hour. Within this time frame both the control and the silver with no resistor allow bacterial growth.

A "killing curve" for Escherichia coli in FIG. 10 shows the killing rate associated with E. coli. The 3MΩ resistor utilized in this circuit corresponds to the smallest current 0.5 uA. The curve shows bacterial reduction from 320*10E6 to zero within five hours, a rate of approximately 72*10E6 bacteria per hour. Within this time period both the control and the silver with no resistor tests continue to support bacterial growth.

EXAMPLE 4

Optimization of Critical Operational Parameters of Antimicrobial Metals

Antimicrobial properties of specific metals or metal forms differ when modifications are made in the experimental parameters. Using data from the "killing curve analyses", critical parameters will be established for the generation of optimal antimicrobial effects, and can then be balanced against the characteristics of the application into which the metal will be incorporated.

In order to evaluate any possible toxicity of antimicrobial metal compositions on mammalian cells, in vitro cell culture systems may be utilized Specifically, batteries and resistors connected in series with a predetermined antimicrobial metal composition is aseptically threaded into a mammalian cell culture flask and allowed to run, generating metal ions within the culture. Cells are monitored during testing for morphological changes and percentages of live vs. dead cells. In addition, treated and control cells may be evaluated via metabolic function assays such as albumin and urea levels in hepatocytes; bone alkaline phosphatase levels in osteoblasts; and matrix protein levels in chrondrocytes.

In addition, the effects of circuit polarity, operation time and duty cycle are evaluated on cells in vitro using device parameters and optimized for maximal antimicrobial effect and low toxicity. An external circuit is constructed allowing for varying run-time cycles and alternating circuit polarities.

The external circuit with battery, resistor, an inverter for reversing polarity, and a timer will be connected in series with the test antimicrobial metal. The circuit will be aseptically threaded into the cell culture flask and allowed to run, generating antimicrobial ions within the culture. The continuous running time of the circuit as well as the polarity of the circuit will be manipulated by varying the circuit timer and changing the polarity of the circuit via the switch.

EXAMPLE 5

In Vivo Evaluation

A rat model for evaluation of the effect of an inventive device implant-related osteomyelitis is described in this example. The model uses a bacterial inoculate to promote infection, as described in Lucke et al. 2003 [please provide this reference]. S. aureus subspecies aureus Rosenbach (ATCC #49230), isolated from a patient with chronic osteomyelitis, and shown to cause bone infections in rats (Solberg 1999) is utilized in this procedure as a model Gram positive organism. The previously tested clinical E. coli isolate serves as the model Gram negative organism.

Aliquots (100 microliters) of S. aureus or E. coli grown overnight in tryptic soy broth (TSB) are transferred to tubes containing 3 ml of sterile TSB. These cultures are grown to log-phase growth. Colony-forming units (CFU) per ml are confirmed by several plate counts using a spiral plating technique. Suspensions in sterile phosphate buffered saline (PBS) are held at −80° C. until the day of surgery. To quantify possible loss of viable bacteria following the freeze-thaw cycle, CFU/ml is confirmed after each cycle of defrosting.

Surgery is performed under general anesthesia by intraperitoneal injection of xylazine 2% (Medistar®, 12 mg/kg body weight) and ketaminehydrochloride (Ketavet, 100 mg/ml; 80 mg/kg body weight). Rats are maintained on inhaled isoflourane.

Animals are prepared for surgery as follows: One leg is shaved and scrubbed with betadine alcohol prep. To prevent accidental bacterial contamination during surgery animals are placed on sterile drapes. Bodies are covered with sterile sheets; the prepped leg is separately draped in a sterile manner. A small incision (5 mm) of skin and fascia at the proximal tibial metaphysis provides access to the tibial periosteum. The medullary cavity of the proximal metaphysis is accessed through cortical and cancellous bone via a 1 mm diameter titanium burr, leaving the surrounding periosteum intact. A steel Kirschner wire, 1.0 mm in diameter, is inserted into the medullary cavity and pushed forward distally for smooth dilatation of the cavity for a length of approximately 32 mm distally, and removed. A 50 microliter microsyringe is inserted into the medullary cavity and used to inject either 10 microliters of sterile PBS, or, PBS containing S. aureus or E. coli in a concentration of $10^3$ CFU/10 microliter. Following inoculation, a 32 mm length of antimicrobial test wire, representing an engineered implant (99.7% purity), or a titanium wire (99.8% purity) representing current implant material, is inserted into the cavity. The protruding portion of the test wire will attach to an external wire making the battery connection complete. The battery, within a battery pack will placed in a rodent jacket fitted to the rat. Within the experimental groups the two groups designated as Ag wire and electric will be identical except for the current that is running through the implant. The delay turn on AG wire and electric group will have the wire implanted and then wait three days before the battery is inserted into the circuit. This delay will allow for full growth of the bacterial inoculums within the rat.

All implants are performed the soft tissue will be irrigated with betadine solution. Skin and fascia are sutured in a single knot. All groups designated as having an electrical current will have a battery inserted into the circuit and the current through the circuit turned on.

Animals are sacrificed at one week, two weeks and four weeks. Post-sacrifice the implants are removed, and the tibia into which the implant is placed is examined for gross infection. Samples are taken from the medullary cavity for culture and histological examination.

To assess development and progression of bone infection radiographs are taken in posterior-anterior and lateral views on Days 0 (OP), 7, 14, 21, and 28. Proximal epi-/metaphysis, diaphysis, and distal epi-/metaphysis are examined for evaluation of infection extent and effect of implant.

EXAMPLE 6

A hip implant having silver disposed on the outer surface according to the present invention is activated to produce silver ions. The activated implant is implanted in agar inoculated with Gram negative bacteria, E. coli. This preparation is placed at 37° C. and observed at various times following inoculation. A "killing zone" is observed around the implant. Similar experiments with Gram positive bacteria and fungus also result in an observed killing zone.

EXAMPLE 7

A hip implant having copper disposed on the outer surface according to the present invention is activated to produce copper ions. The activated implant is implanted in agar inoculated with Gram positive bacteria, MRSA. This preparation is placed at 37° C. and observed at various times following inoculation. A "killing zone" is observed around the implant.

EXAMPLE 8

A hip implant having copper and silver disposed on the outer surface according to the present invention is activated to produce copper and silver ions. The activated implant is implanted in agar inoculated with both Gram negative and Gram positive bacteria, E. coli and MRSA. This preparation is placed at 37° C. and observed at various times following inoculation. A "killing zone" for both Gram positive and Gram negative organisms is observed around the implant. In similar experiments, a fungus, Candida albicans is used to inoculate the medium and is also inhibited by the activated implant.

EXAMPLE 9

A hip implant having cadmium, copper and silver disposed on the outer surface according to the present invention is activated to produce copper and silver ions. The activated implant is implanted in agar inoculated with multiple microbial organisms including Gram negative and Gram positive bacteria, E. coli and MRSA, as well as Candida Albicans. This preparation is placed at 37° C. and observed at various times following inoculation. A "killing zone" for all organisms is observed around the implant.

Any patents or publications mentioned in this specification are incorporated herein by reference to the same extent as if each individual publication is specifically and individually indicated to be incorporated by reference.

Patents, patent applications, or publications mentioned in this specification are incorporated herein by reference to the same extent as if each individual document was specifically and individually indicated to be incorporated by reference. In particular, U.S. patent application Ser. No. 11/172,138, filed Jun. 30, 2005 and U.S. Provisional Patent Application Ser. No. 60/708,320, filed Aug. 15, 2005, the entire content of each of which is incorporated herein by reference.

The compositions, methods and apparatus described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

We claim:

1. A medical device, comprising:
   a body having an external surface;
   an antimicrobial material disposed on the external surface of the body; and
   a current generator connected to the body such that a flow of antimicrobial ions is created from the antimicrobial material into a conductive medium adjacent the external surface of the body.

2. The medical device of claim 1, wherein said current generator comprises:
   a power source including a first element and a second element, wherein at least one of the first element and the second element is in electrical communication with the antimicrobial material such that the ion flow is created when a current path is established that includes the power source and at least a part of the antimicrobial material.

3. The medical device of claim 2, further comprising:
   an insulator that allows the current path to be established by forcing the ion flow into the conductive medium adjacent the implant body.

4. The medical device of claim 3, wherein the insulator is configured to prevent current flowing from the first element from reaching the second element without completing a circuit including the conductive medium adjacent to the external surface of the body.

5. The medical device of claim 3, wherein the antimicrobial material is disposed on a portion of the external surface of the implant body ranging from 1-100% of the external surface of the implant body, excluding any portion of the external surface occupied by the insulator.

6. The medical device of claim 3, wherein the antimicrobial material is disposed on a portion of the external surface of the body ranging from 50-99% of the external surface of the body, excluding any portion of the external surface occupied by the insulator.

7. The medical device of claim 3, wherein the antimicrobial material is disposed as at least two regions of coating on the external surface of the body, at least one region of coating in electrical communication with the first terminal and at least one region of coating in electrical communication with the second terminal,
   wherein the insulator is placed in the current path between the first terminal of the power source and the second terminal of the power source, and
   wherein the insulator electrically insulates the at least two regions of coating from each other.

8. The medical device of claim 1 wherein the antimicrobial material is a metal.

9. The medical device of claim 1 wherein the antimicrobial material is a metal-doped material.

10. The medical device of claim 1 wherein the body is tubular in shape.

11. The medical device of claim 1, wherein the body includes:
    an internal cavity having a wall and an opening; and
    a cap removably disposed in the opening of the internal cavity, wherein the power source is disposed in the internal cavity.

12. The medical device of claim 11, further comprising a metal component disposed on a portion of the internal cavity wall.

13. The medical device of claim 1, wherein the antimicrobial material is selected from the group consisting of: silver; copper; both silver and copper; both silver and cadmium; both copper and cadmium; and a combination of silver, copper and cadmium.

14. The medical device of claim 1, wherein the antimicrobial material is selected from the group consisting of: gold, zinc, cobalt, nickel, platinum, palladium, manganese, chromium; and a combination thereof.

15. The medical device of claim 1, wherein the antimicrobial material ranges in thickness between $1 \times 10^{-9}$-$5 \times 10^{-3}$ meters.

16. The medical device of claim 1, wherein the medical device is configured to be temporarily or permanently implanted within a patient.

17. The medical device of claim 1, wherein the conductive medium comprises conductive body tissue or fluid.

* * * * *